(12) United States Patent
Storti et al.

(10) Patent No.: US 9,938,390 B2
(45) Date of Patent: Apr. 10, 2018

(54) METHOD FOR THE PREPARATION OF MACROPOROUS PARTICLES AND MACROPOROUS MICROCLUSTERS

(71) Applicant: ETH ZURICH, Zurich (CH)

(72) Inventors: Giuseppe Storti, Zurich (CH); Massimo Morbidelli, Zurich (CH); Miroslav Soos, Bulach (CH); Alexandros Lamprou, Zurich (CH); Bastian Brand, Zurich (CH)

(73) Assignee: ETH ZURICH, Zurich (CH)

( * ) Notice: Subject to any disclaimer, the term of this patent is extended or adjusted under 35 U.S.C. 154(b) by 0 days.

(21) Appl. No.: 14/439,438

(22) PCT Filed: Nov. 22, 2013

(86) PCT No.: PCT/EP2013/003532
§ 371 (c)(1),
(2) Date: Apr. 29, 2015

(87) PCT Pub. No.: WO2014/079580
PCT Pub. Date: May 30, 2014

(65) Prior Publication Data
US 2015/0291760 A1  Oct. 15, 2015

(30) Foreign Application Priority Data

Nov. 26, 2012 (EP) .................... 12007949

(51) Int. Cl.
| | |
|---|---|
| *C08J 9/228* | (2006.01) |
| *C08F 212/08* | (2006.01) |
| *C08F 2/22* | (2006.01) |
| *C08J 9/16* | (2006.01) |
| *C08F 2/00* | (2006.01) |
| *B01D 15/36* | (2006.01) |
| *B01J 41/14* | (2006.01) |
| *B01J 41/20* | (2006.01) |
| *C07K 1/16* | (2006.01) |

(52) U.S. Cl.
CPC ............ *C08J 9/228* (2013.01); *B01D 15/361* (2013.01); *B01J 41/14* (2013.01); *B01J 41/20* (2013.01); *C07K 1/16* (2013.01); *C08F 2/001* (2013.01); *C08F 2/22* (2013.01); *C08F 212/08* (2013.01); *C08J 9/16* (2013.01); *C08J 2205/04* (2013.01); *C08J 2325/06* (2013.01); *C08J 2331/04* (2013.01); *C08J 2333/00* (2013.01); *C08J 2333/06* (2013.01)

(58) Field of Classification Search
CPC . C08J 9/16; C08J 9/228; B01D 15/361; B01J 41/14; B01J 41/20; C07K 1/16; C08F 2/001; C08F 2/22
See application file for complete search history.

(56) References Cited

FOREIGN PATENT DOCUMENTS

WO  2009/043191 A2  4/2009

OTHER PUBLICATIONS

Miroslav Soos et al., "Effect of shear rate on aggregate size and morphology investigated under turbulent conditions in stirred tank", Journal of Colloid and Interface Science, 2008, pp. 577-589, vol. 319.
Amgad S. Moussa et al., "Effect of Solid vol. Fraction of Aggregation and Breakage in Colloidal Suspensions in Batch and Continuous Stirred Tanks", Langmuir, 2007, pp. 1664-1673, vol. 23, No. 4.
Delong Xie et al., "Criticality for shear-induced gelation of charge-stabilized colloids", Soft Matter, The Royal Society of Chemistry, 2010, pp. 2692-2698, Vo. 6.
International Search Report for PCT/EP2013/003532 dated Jan. 20, 2014.

*Primary Examiner* — Edward J Cain

(74) *Attorney, Agent, or Firm* — Sughrue Mion, PLLC

(57) ABSTRACT

A method for producing macro porous micro-clusters is proposed comprising at least the following individual steps in given order: a) synthesis of dispersed cross-linked polymeric latex primary particles starting from at least one monomer or oligomer using emulsion polymerization; b) swelling of the primary particles with a liquid comprising at least an additional charge of monomer and/or oligomer and a cross-linker, optionally further comprising functionalization agents; c) destabilization by increase of ionic strength (by adding a salt and/or acid and/or base) in a combination with application of shear, both being above the gel formation boundary of the phase diagram, until agglomerates composed of primary particles of the desired size are formed; d) polymerization of the agglomerates to form the macro porous micro-clusters. Furthermore the invention to relates to correspondingly produced micro-clusters and uses of such micro-clusters in particular for chromatographic purposes.

49 Claims, 12 Drawing Sheets a)

b)

c)

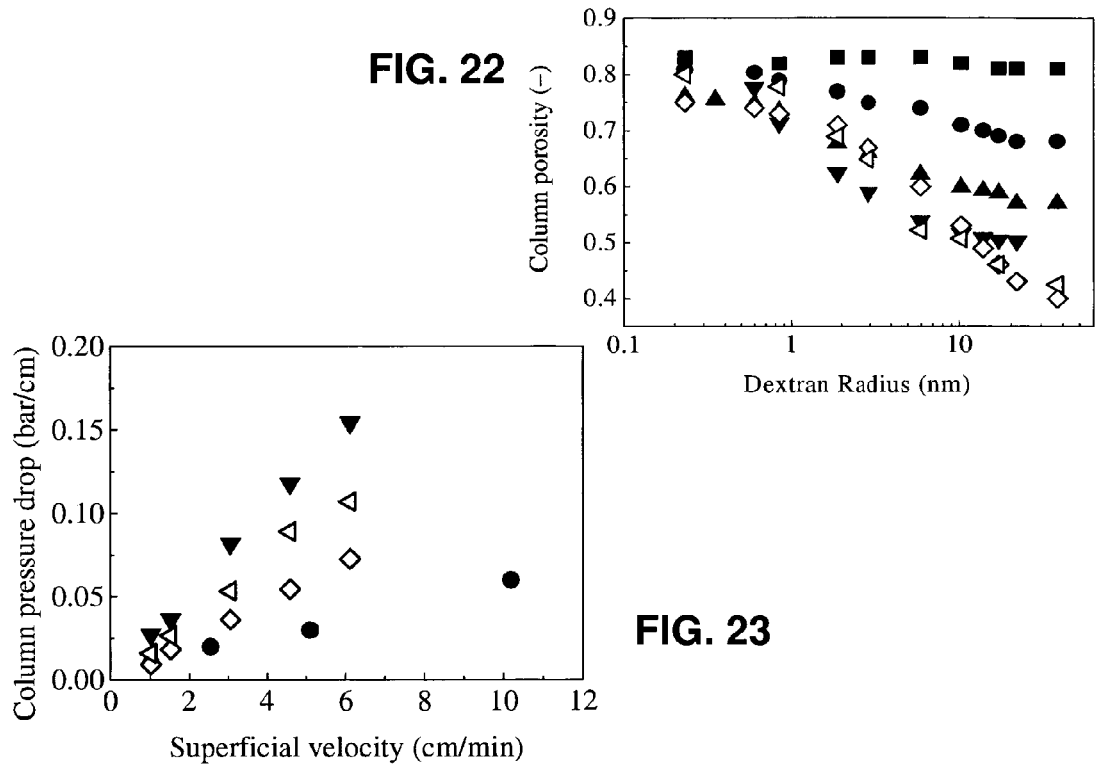
FIG. 22
FIG. 23
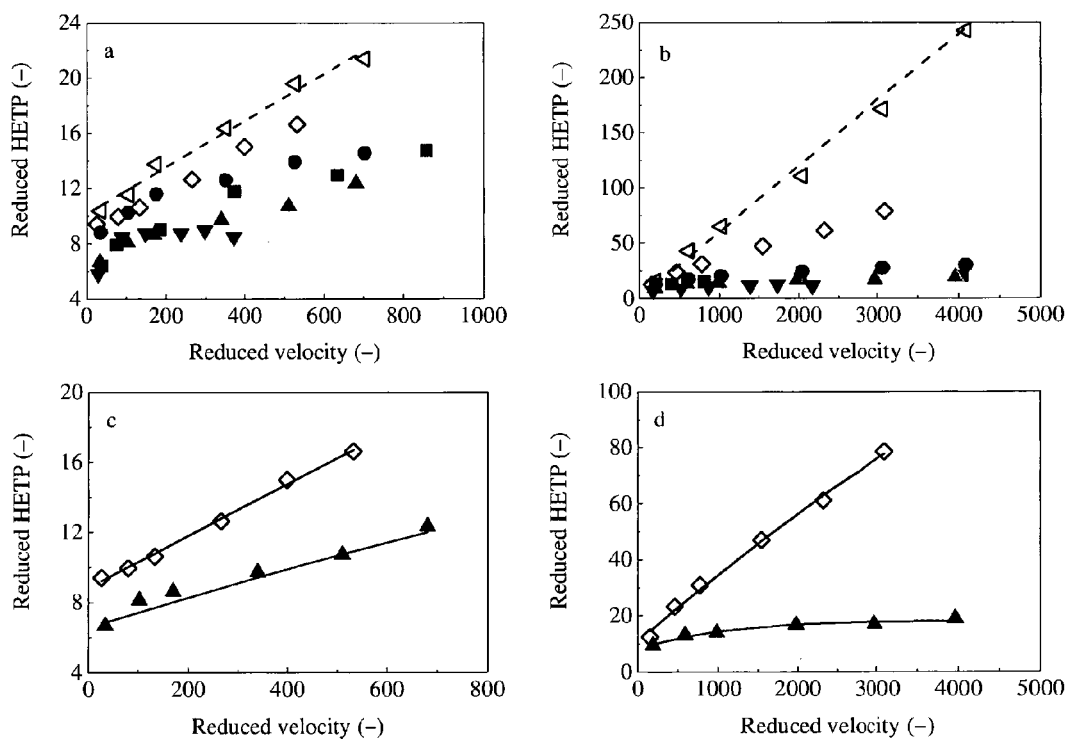
FIG. 24

METHOD FOR THE PREPARATION OF MACROPOROUS PARTICLES AND MACROPOROUS MICROCLUSTERS

CROSS REFERENCE TO RELATED APPLICATIONS

This application is a National Stage of International Application No. PCT/EP2013/003532 filed Nov. 22, 2013, claiming priority based on European Patent Application No. 12 007 949, filed Nov. 26, 2012, the contents of all of which are incorporated herein by reference in their entirety.

TECHNICAL FIELD

The present invention relates to methods for the preparation of macroporous particles, macroporous particles obtained using such methods as well as to uses of such macroporous particles.

PRIOR ART

The synthesis of macroporous copolymer resins has been extensively investigated. Applications of porous resins include among others solid-phase synthesis, extraction, ion exchange, catalysis, pollutant adsorption, chromatography and insulators.

Irrespectively of how sophisticated the synthetic procedure is, a pore-generating system is typically employed in the production of macroporous polymer resins. This may be a traditional inert porogen for generic applications, or a specifically-interacting template for specific applications, e.g. affinity matrixes. In the first case, a good or a poor solvent for the incipient polymer network, a non-reactive linear polymer or a combination of the three can be applied. While initially the porogenic mixture forms a single phase with the monomer and the crosslinker, at some point during the course of polymerization phase separation of the growing polymer network occurs, which might be either due to extensive crosslinking or simply to porogen-polymer matrix incompatibility. The polymeric nuclei thus formed organize themselves into microspheres, which subsequently come together into larger agglomerates that constitute the main building blocks of the final polymer network. The resulting pores are ultimately filled with the porogen, which is eventually extracted with an appropriate solvent or series of solvents at the end of the polymerization. The resulting pore morphology, pore size distribution and specific surface area depend on the amount and composition of the porogenic mixture, crosslinker, temperature and time of polymerization, as well as whether the polymerization is run in a dispersed system or in bulk. Obviously dispersed systems yield particles (typically micron-sized), while bulk systems yield continuous monoliths.

Despite the growing scientific attention to monoliths, their commercial application remains limited. For example, in the area of chromatography, there are limited examples of commercially available monolithic stationary phases, with particles being still the most widespread packing material. For the production of particulate resins several methods have been employed, ranging from simple surfactant-free dispersion polymerization to classical suspension polymerization or more elaborate procedures. Examples of the latter include activated swelling, seeded emulsion polymerization and staged templated suspension polymerization. Novel porogens including oligomers, ionic and steric surfactants, and others have also been proposed. Yet, in all cases the relation between the factors affecting the pore generation and properties of the final material is still not well understood and require a good deal of empiricism.

Reactive Gelation is an alternative, porogen-free method towards macroporous monoliths. It is based on the colloidal principle of stagnant Reaction-Limited Cluster Aggregation (RLCA), i.e. the aggregation of polymer particles in a stagnant suspension, partially destabilized by the addition of salt and/or acid at a concentration below the suspension's Critical Coagulation Concentration (CCC). The product is a colloidal particle gel, which is a space-filling, percolating network of weakly interconnected particles with a fractal structure. Prior to gelation the latex particles are swollen by a well-defined amount of a monomeric mixture containing a thermal radical initiator. This treatment softens the polymer particles, at least close to their surface. After the gel formation in the stagnant reaction medium the temperature is raised, inducing polymerization of the swelling monomers and a further rearrangement of the network structure, along with a substantial increase of its mechanical strength. The major novelty of the procedure of Reactive Gelation is this last step, normally referred to as "post-polymerization". It has been shown by N2 sorption and SEM analyses, that varying the amount of monomers added during the swelling step and the crosslinking degree along the primary particle radius allows controlling the surface area, pore size and rigidity of the final porous material. The resulting material is a macroporous monolith, which can be used for HPLC applications, either in the form of ground and size-classified polystyrene particles packed in a conventional column or as a single monolithic PMMA column. No size exclusion during Inverse Size-Exclusion Chromatography (ISEC) experiments and attractive mass transport properties by Van Deemter analysis has so far been demonstrated.

SUMMARY OF THE INVENTION

This invention proposes a new and unexpectedly efficient, porogen-free production method for the production of rigid macroporous microparticles with tailorable properties by in essence combining aggregation and post-polymerization under proper shear conditions.

Similarly to the above mentioned Reactive Gelation process performed under stagnant conditions, the preparation of the porous material is divided into distinct, successive steps: latex preparation; latex swelling; post-polymerization.

However between the step of latex swelling and the one of post-polymerization according to the invention a further step of controlled latex aggregation and breakage is implemented leading to microcluster structures with well defined properties.

So the main differences to stagnant Reactive Gelation lie in the aggregation step, which is realized under shear conditions. Depending on the primary particles destabilization, which is realized either by complete or partial screening of the electrostatic repulsion so aggregation of the primary particles occurs under fully destabilized conditions, i.e. in a so called Diffusion-Limited Cluster Aggregation (DLCA), or under partially destabilized conditions, i.e. Reaction-Limited Cluster Aggregation (RLCA), both in the presence of shear. The destabilization is achieved by increase of ionic strength (by adding a salt and/or acid and/or base) in a combination with application of shear, both being above the gel formation boundary of the phase diagram, until agglomerates composed of primary particles of the desired size are formed. This aggregation leads to the formation of clusters, which grow in size until they start being affected, i.e. broken by the shear. Subsequently, the system evolves through multiple aggregation-breakage events, which eventually lead to steady-state conditions. A dispersion of particles in the micrometer size range is thus obtained, the size of which is determined by this dynamic equilibrium between aggregation and breakage, referred to in the following as microclusters.

This controlled aggregation phenomenon as such has already been reported in the literature e.g. in the article by Soos et al (Soos, M.; Moussa, A. S.; Ehrl, L.; Sefcik, J.; Wu, H.; Morbidelli, M., Effect of shear rate on aggregate size and morphology investigated under turbulent conditions in stirred tank. Journal of Colloid and Interface Science 2008, 319 (2), 577-589), Moussa et al (Moussa, A. S.; Soos, M.; Sefcik, J.; Morbidelli, M., Effect of solid volume fraction on aggregation and breakage in colloidal suspensions in batch and continuous stirred tanks. Langmuir 2007, 23 (4), 1664-1673) or Xie et al (Xie, D. L.; Wu, H.; Zaccone, A.; Braun, L.; Chen, H. Q.; Morbidelli, M., Criticality for shear-induced gelation of charge-stabilized colloids. Soft Matter 2010, 6, (12), 2692-2698). However all these investigations were on a purely theoretical basis, so the only idea was to analyze the effect of shear rate on aggregate size and morphology of particles, the effect of solid volume fraction on aggregation and breakage etc., but in these investigations the aggregates were not intended to and were also never subjected to a post-polymerization process. Since in these investigations anyway only solid particles have been used which do not allow for such a post-polymerization step, such an additional step would also from a principal viewpoint not have been possible under the circumstances.

It is well-accepted that colloidal aggregates, although exhibiting a disordered structure, are actually self-similar objects, obeying the fractal geometry. This means that independent of the length scale used during their characterization, their mass scales with their size following a certain power law, with a scaling exponent called the fractal dimension, $d_f$, which indicates how compact the internal aggregate structure is. Here, it should be noted that this is universally applicable, including both aggregation mechanisms discussed in the context of this work: the production of colloidal gels via RLCA under stagnant conditions, as well as that of clusters via RLCA and/or DLCA under shear, whereby multiple aggregation and breakage events occur.

In the proposed approach, similarly to the above outline of stagnant Reactive Gelation, primary particles are subjected to swelling treatment with a monomeric mixture prior to aggregation, while post-polymerization is employed to rigidify the initially fragile aggregates. The porosity and internal porous structure of the resulting clusters likely arises through a combination of four different densification mechanisms, which qualitatively described are: cluster breakup, inter-particle coalescence, polymerization-induced shrinkage and surface energy-induced rearrangement. Firstly, breakage and restructuring of a fractal aggregate gives rise to denser structures of higher fractal dimension. Secondly, the initial latex nanoparticles are in a glassy state, i.e. rigid, at room temperature, however they are made to absorb a finite amount of water-insoluble monomers. Such swelling treatment can lower their glass transition temperature, creating rubbery domains especially close to their surface. Rubbery particles coalesce during aggregation, a process which is responsible for increasing the fractal dimension both under quiescent DLCA and shear-induced aggregation. Further compactification is definitely occurring during post-polymerization. Lastly, highly probable is also the structural rearrangement/densification similar to the one taking place during sintering of inorganic materials, driven by the minimization of the curved interfacial area of the nanoparticles comprising the clusters. Therefore, the final densification extent can be controlled by acting upon the multiplicity of the aggregation and breakage events themselves, or by acting upon the coalescence extent of the softened primary particles. Softer particles coalesce to a larger extent, while the softening induced by swelling depends in turn to the particles' crosslinking degree. In this regard, we have here chosen to vary the crosslinking degree along the primary particle radius by growing of single or multiple (e.g. two successive) shells on the primary particles core during latex preparation under starved feeding conditions. Thus, the radial composition of these shells is independent of monomers and radicals reactivity. Moreover, surface functionalization is possible e.g. following common practice with polymer materials, in this respect the disclosure of WO2009/043191 is included. Specifically, having incorporated in the outer shell a co-monomer which can initiate Atom Transfer Radical Polymerization (ATRP) from the clusters surface, functionalization with grafted polymer chains is possible at a later stage. Another possibility to functionalize the surface of formed clusters is to decorate it small particles, e.g. with oppositely charged very small particles (nanoparticles, applied e.g. as a gel), i.e. for example using small negatively charged particles when positively charge clusters are used and vice versa.

The important steps are schematically visualized in FIG. 1.

More generally speaking, the present invention relates to a method for producing macro porous micro-clusters comprising at least the following individual steps and preferably in given order:

a) synthesis of dispersed cross-linked polymeric latex primary particles starting from at least one monomer or oligomer in an emulsion polymerization (inclusive of mini-emulsion polymerization);

b) swelling of the primary particles with a liquid comprising at least an additional charge of monomer and/or oligomer and/or a cross-linker, optionally further comprising functionalization agents;

c) swollen particles destabilization by increase of ionic strength (by adding a salt and/or acid and/or base) in a combination with application of shear until agglomerates composed of primary particles of the desired size are formed, in particular destabilization, preferably by adding a salt and/or acid and/or base, preferably in an extent such that its concentration in a suspension comprising the particles is above the critical coagulation concentration, and concomitant application of shear until agglomerates of the particles of the desired size are formed;

d) polymerization of the agglomerates to form the macro porous micro-clusters.

Preferably step a) is carried out as follows:

The monomers and/or oligomers as used in step a) and/or b) are those which form nanoparticles using emulsion or mini-emulsion based methods. Preferably they are based on styrene and/or acrylic monomers and/or vinyl acetate, or their derivatives. Possible systems are e.g. given in Lovell P. A. and El-Aasser, M. S. (Editors), 1997, Emulsion Polymerization and Emulsion Polymers, Wiley, Chichester, West Sussex, England.

According to yet another preferred embodiment of the proposed invention in step c) for the destabilization an appropriate balance of shear and/or ionic strength (by addition of salt and/or acid and/or base) should preferably be established. If higher shear is applied, a lower ionic strength is possible, and vice versa. Functionally speaking, this can be expressed in terms of a phase diagram where for given ionic strength shear rate equal or larger than the critical value has to be applied. Such phase diagram is readily obtained from measurement of the critical ionic strength value for no shear, the critical shear value for no salt/acid/base as well as at least one ionic strength value for a determined shear or at least one critical shear value for a determined ionic strength. Consequently a phase boundary is determined from these values using a numerical, preferably quadratic fitting, in particular to determine the parameters a, b and c of the formula, wherein S is the shear rate and I is the ionic strength:

$$S_{fit}=a\ I^2+b\ I+c$$

and selecting the shear rate (S) and the ionic strength (I) for step c) such that $$S(I) \geq S_{fit}(I).$$

The shear can be applied by stirring in a corresponding container, or it can be generated by flow through a corresponding mixing device. According to a preferred embodiment, the shear in step c) is generated by passing the fluid through at least one micro-channel, wherein preferably this micro-channel is a device such as a Homogenizer HC-5000 (Microfluidics, USA) with a z-shape microchannel of a rectangular cross-section (with a length of $5.8 \times 10^{-3}$ m and cross-sectional area of $5.26 \times 10^{-8}$ m2), referred to as z-MC. Intense shear, up to $1.7 \times 10^6$ l/s at 170 bar with water (manufacturer specification) in the z-MC is generated by forcing the colloidal system to pass through such z-MC under pressure. Generally speaking structures with a z-shape, preferably of a rectangular cross-section, e.g. with a length of $3 \times 10^{-3}$-$7 \times 10^{-3}$ m, and a cross-sectional area of $3 \times 10^{-8}$-$7 \times 10^{-8}$ m$^2$, can be chosen. This e.g. under conditions of up to $1.7 \times 10^6$ l/s at up to 170 bar. How step c) is actually carried out can be used for tailoring the properties of the resultant micro-clusters. One important aspect in this respect is the tuning of the shear rate in an appropriate range, such that under steady-state shear conditions agglomerates of the desired size and properties are obtained. According to a preferred embodiment concerning this aspect in step c) when shear DLCA conditions are considered a shear rate in the range of 200-4000 l/s, preferably in the range of 300-3000 l/s is applied. In the case of shear induced RLCA conditions a shear rate in the range from $1 \times 10^5$ to $1.7 \times 10^6$ l/s, preferably from $5 \times 10^5$ up to $1.7 \times 10^6$ l/s is applied.

Another important parameter within step c) is the adjustment of the ionic strength (by addition of salt/acid/base, ionic strength can be defined via concentration) important for the aggregation. According to a preferred embodiment concerning this aspect when aggregation is performed under shear DLCA conditions in step c) the salt/acid/base concentration, at least at the end of the step, is twice as high as the critical coagulation concentration, preferably five times as high as the critical coagulation concentration, most preferably 10 times as high as the critical coagulation concentration (CCC).

In step c) when aggregation is performed under shear DLCA conditions the salt/acid/base concentration can be held constant over the whole step, however it can also be increased over time, preferably by applying at least two successive gradient salt/acid/base addition steps. Preferentially already the first adding of salt/acid leads to a concentration of the salt/acid in the suspension above the critical coagulation concentration. Also possible is a continuous increase of the salt/acid concentration or the increase along the specifically tailored concentration profile. According to yet another preferred embodiment, step c) can be carried out for a time span of at least 5 minutes, preferably at least 8 minutes, 10 minutes or 30 minutes, preferably of at least 60 minutes, most preferably for a time span of in the range of 30-300 minutes.

According to yet another preferred embodiment, step c) when shear-induced RLCA conditions are applied the salt/acid/base concentration should preferably be below the critical coagulation concentration (CCC), preferentially in the range of salt/acid/base concentration between 1/10 to 1/2 CCC and most preferably in the range from 1/4 to 1/3 CCC. To eliminate undesired aggregate formation which can block the microchannel, salt/acid/base solution with concentration equal to or lower than corresponding CCC is mixed with the latex solution.

According to a preferred embodiment as concerns the step of post-polymerization, step d) is carried out for a time span of at least 1 hour, preferably of at least five hours, most preferably of at least 10 hours, wherein further preferably a temperature of at least 50° C., preferably of at least 60° C. is used in the suspension.

The primary particles are preferably core shell particles with a hard core, which preferably is at least 10% cross-linked, preferably at least 15% cross-linked, and a soft shell, which is preferably at most 7% cross-linked, preferably in the range of 1-5% cross-linked.

Further preferably the diameter of the primary particles is in the range of 500-200 nm, most preferably in the range of 75-180 nm, and wherein the core diameter of the primary particles is in the range of preferably 40-160 nm, most preferably in the range of 70-150 nm.

According to yet another preferred embodiment of the proposed invention in step b) a mixture of monomers or oligomers, preferably of the same or at least similar type as the ones used in step a), together with a cross-linker system, preferably in approximately the same amount as the monomers/polymers, most preferably chosen to be a system such as divinylbenzene (in particular for styrene) and/or EGDMA (Ethyleneglycoldimethacrylate in particular for PMMA), and optionally with a functional initiator, is added, preferably drop wise added to the suspension obtained in step a).

In step c) preferentially a solid volume fraction below 10%, preferably below 9%, most preferably in the range of 1-9% is used. This in particular if aggregation is performed under fully destabilized Diffusion-Limited Cluster Aggregation (DLCA) conditions.

In step c) also a solid volume fraction below 50%, preferably below 30%, most preferably in the range of 5-25% can be used, in particular if aggregation is performed under partially destabilized Reaction-Limited Cluster Aggregation (RLCA) conditions.

According to yet another preferred embodiment and as already pointed out above the generated macro porous micro-clusters are surface functionalized, wherein this surface functionalization is particularly preferable if it is pronounced in the pockets of the porous particles. Procedures similar to those disclosed in WO2009/043191 can be used to generate the surface functionalization by grafting of a functional groups onto the surface of the macro porous microclusters. This grafting in case of chains of functional groups can either take place by grafting corresponding oligomeric groups onto the surface of the particles, or the chains can be generated by polymerisation directly on the surface. One preferred method is flow-through Atom-Transfer Radical Polymerization (ATRP). According to a preferred embodiment, the surface functionalization is generated by the functionalization agent present during a step b) and/or by a surface functionalization step carried out before or after step d), preferably after step d). The surface functionalization may comprise or consists of charged polymeric groups or polyelectrolyte groups, which are preferably branched and in the form of brushes. Examples of such charged polymeric groups are sulphonate groups, phosphate groups, polyamine groups, e.g. (2-Acrylamido-2-methylopropane sulphonic acid) (AMPS), [2-(Acryloyloxy)ethyl]trimethylammonium chloride (ATMA), N-isopropylacrylamide (NIPAM) containing several charged group on a single chain particularly preferably with a branched multiple group brushes.

The generated macro porous micro-clusters can also be coated, in particular by filling cavities thereof, by a functional substance, e.g. a functional gel, preferably by a functional gel for ion exchange chromatography, preferably for anion exchange chromatography, wherein most preferably the functional gel is an aminated styrene- or acrylate-based polymer with which particles are impregnated after step d).

The invention furthermore relates to macro porous micro-clusters as obtained or as obtainable by a method as outlined above. Preferably these micro-clusters are characterized by a fractal dimension of at least 2.0 or at least 2.2, preferably of at least 2.3, most preferably of at least 2.5, and in particular in the range of 2.3-3 or 2.5-3.

The micro-clusters are further preferably characterized in that they are comprising essentially only macro pores, so that they are essentially free from pores with a size below 20 nm, preferably in that it is essentially free from pores with a size below 40 nm, preferably essentially free from pores with a size below 50 nm.

As concerns the size of these micro-clusters, they preferably have a radius of gyration in the range of 10-100 μm and/or a surface area SBET in the range of 5-30 m$^2$ per gram.

Last but not least the present invention relates to uses of such micro-clusters. In particular it relates to uses for the separation of chemical compounds, in particular small ions (cations or anions) with molecular weight in the range of 10-200 Dalton or biopharmaceuticals, preferably with large molecular weight in the range of 10 000-1 000 000 Dalton (e.g. peptides or monoclonal antibodies) In such applications, preferably the micro-clusters are either directly or after grinding used for chromatographic separation purposes.

Further embodiments of the invention are laid down in the dependent claims.

In summary, the following important aspects can be identified:
  A new procedure for producing macroporous particulate resins, which does not include the use of any porogen, is made available.
  This procedure comprises of a series of well-defined, sequential steps: latex preparation, latex swelling, latex aggregation-cluster breakage and post-polymerization.
  The pores do not come into existence from a phase separation event, but rather from the aggregation of prefabricated nanoparticles, which constitute the structural units of our macroporous network. Actually, their composition can be definitively controlled during the latex preparation, since the thermodynamic and kinetic aspects of the polymerization are largely decoupled from the pore formation mechanism. Therefore, there is no need to introduce large amounts of agents foreign to the polymerization so as to generate pores.
  The pores generated are unusually large, i.e. in the micrometer range, while micropores are absent. Arguably, depending on the applied aggregation procedure (DLCA under shear/RLCA under shear) the achieved pore size distributions can be tuned from rather broad to very narrow and having an average size from micro to macropores. The formation of micropores is actually inherent to the classical mechanism, as they are essentially the voids in between the initially precipitated polymeric "nuclei". The second level of organization of the classical macroporous domain, the "microspheres", are 100-200 nm in size and are the ones containing the micropores. The "microspheres" size corresponds closely to the size range of the structural units of our macroporous network, the primary particles, with the chief difference that our primary particles are non-porous. This, together with the primary particle fusion, explains the absence of micropores in our case, which is very crucial for certain applications, like chromatography of large biomolecules. Moreover, the presence of very large pores, with favorable connectivity and expectedly also permeability, is advantageous for such applications, especially if subsequent surface grafting is applied, that could induce certain pore narrowing. Actually, the presence of MCA (methyl α-chloroacrylate) on the pore surface can serve precisely the purpose of functionalization via surface-initiated ATRP (atomic transfer radical polymerization), a highly-versatile living polymerization technique, allowing a range of specialty applications to be targeted. Another approach which can be used for surface functionalization is surface decoration by a functional gel (very small polymeric nanoparticles) which strongly increase the number of ion-exchange sites per surface area because the gel particles are permeable for small ions, thus making use of the entire particle volume.
  The sequential character of the proposed approach allows for the independent control of different parameters along the procedure, which in turn determine the final porous structure, as opposed to the conventional single-step approach for producing macroporous resins. In particular, the primary latex particles are pivotal to the resulting material. By decreasing the rigidity, i.e. by progressively decreasing the crosslinking degree along the particle radius, more compact, larger clusters, with smaller porosities and smaller surface areas are obtained. Decreasing the primary particles size brings about the same effect in compactness, size and porosity, albeit larger surface areas are obtained. The pore size distribution again appears narrower, with pronounced small pore sizes by roughly one order of magnitude. The operating parameters during aggregation and breakage are also of relevance. Increasing the applied shear rate does not affect the internal cluster structure. Yet, it decreases the cluster size and porosity in a trend, while the pore size distributions shift to smaller pore sizes.
  The marked differences between the particulate micro-clusters and a monolith from stagnant reactive gelation are the more open fractal structure of the monolith, along with, in some cases, its considerably narrower pore size distribution.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 22 shows the column porosity values as a function of the dextran radius used in the SEC measurements, wherein Perf 0 (=), Perf 1 (●), Perf 2 (▲), Perf 3 (▼), Poros 50HS (◇) and Fractogel EMD SO3 (M) (◁)

FIG. 23 shows the normalized column pressure drop values ΔP/L as a function of the superficial velocity for the columns, Perf 1 (●), Perf 3 (▼), Poros 50HS (◇) and Fractogel EMD SO3 (M) (◁)

FIG. 24 shows the Van Deemter plots in reduced form for saccharose (a and c) and HSA (b and d) under non-adsorbing conditions for Perf0 (■), Perf1 (●), Perf2 (▲), Perf3 (▼), Poros 50HS (◇) and Fractogel EMD SO3 (M) (◁). The points represent experimental results. The dotted lines represent the fitting with Eq.(1) and Eq.(2) (non-perfusive) for Fractogel EMD SO3 (M) and the solid lines the fitting with theoretical analytical models (perfusive) for Perf2 and Poros 50HS

DESCRIPTION OF PREFERRED EMBODIMENTS

Figure 1:
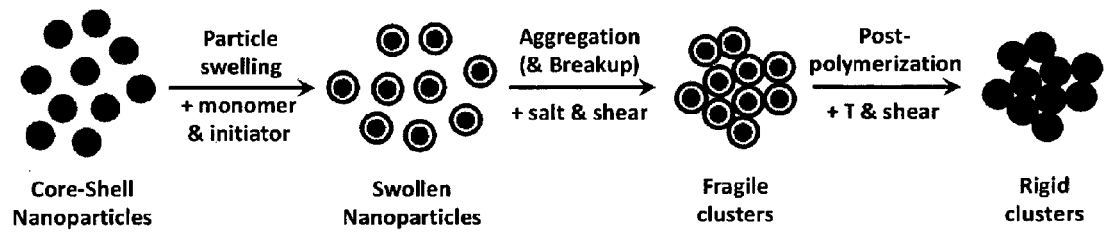
FIG. 1 shows a scheme of the macroporous polymeric clusters synthesis

In the following, a series of in particular polystyrene-based particulate resins are prepared in order to investigate the effect of initial latex properties, namely primary particle size, crosslinking degree along the particle radius and operating parameters, namely applied shear rate, on the final characteristics. In particular, the particle size distribution, the surface morphology, the specific surface area, the pore volume and pore size distribution have been investigated. For the sake of comparison a monolith was also produced by stagnant reactive gelation and subsequently characterized in the same way.

Materials:

All chemicals were used as received. Styrene (St, Fluka, >99%), 4-vinylbenzyl chloride (Aldrich, 90%), methyl methacrylate (MMA, ABCR, 99%), glycidyl methacrylate (GMA, TCI, >95%), vinyl acetate (VAc, Aldrich, >=99%), the crosslinkers divinylbenzene (DVB, Fluka, ~80%) and ethylene glycol dimethacrylate (EGDMA, Merck, for synthesis) and the functional ATRP initiator methyl α-chloroacrylate (MCA, Acros, 99%) as monomers, 2,2'-Azobisisobutyronitrile (AIBN, Aldrich, >98%) or potassium per sulfate (KPS, Fluka, puriss p.a.) as initiators, hexadecane (HD, ABCR, 99%) as hydrophobe, sodium dodecyl sulfate (SDS, Fluka, >96%) as surfactant and magnesium chloride hexahydrate (MgCl2.6H2O, Fluka, >98%) as aggregation inducer. For functionalisation, 2-dimethylaminoethanol (Fluka, >=98%) and sulphuric acid (Sigma, 95-97%) were used. Deionized water was further treated by a Millipore Simpack® purification device.

Analytical Tools:

For gravimetrically determining conversion and final latex dry fraction a HG53 Mettler-Toledo Moisture Analyzer was used. The average size of primary particles was determined by Dynamic Light Scattering—DLS (Malvern Zetasizer Nano ZS). The same device was used to measure the electrophoretic mobility of primary particles and estimate the corresponding ζ potential through the Smoluchowski model. Furthermore, the $MgCl_2$ CCC was experimentally determined for every latex by monitoring the aggregation kinetics under quiescent conditions. To capture the early onset of aggregation each experiment was carried out at solid volume fraction of using DLS.

Since the clusters produced are at the micrometer range, their size and internal structure was characterized by Static Light Scattering—SLS (Malvern Mastersizer 2000). The scattered light intensity, I(q), was used to evaluate the average structure factor of the cluster population, $\langle S(q) \rangle$:

$$\langle S(q) \rangle = \frac{I(0)P(q)}{I(q)} \qquad (1)$$

where I(0) represents the zero-angle intensity, P(q) the form factor (due to primary particles) and q the scattering vector amplitude, defined as:

$$q = 4\pi \frac{n}{\lambda} \sin\left(\frac{\theta}{2}\right) \qquad (2)$$

where θ is the scattering angle, n the refractive index of the dispersing fluid and λ the laser wavelength in vacuum. Using the Guinier approximation for $\langle S(q) \rangle$, which reads:

$$\langle S(q) \rangle = \exp\left(-\frac{q^2 \langle R_g^2 \rangle_{S(q)}}{3}\right), \text{ for } q\langle R_g \rangle_{S(q)} < 1 \qquad (3)$$

the root-mean square radius of gyration of an aggregated population was evaluated applying:

$$\langle R_g^2 \rangle = \langle R_g^2 \rangle + \langle R_{g,p}^2 \rangle \qquad (4)$$

and using $R_{g,p} = \sqrt{3/5} R_p$ for the radius of gyration of primary particles. It is worth noting that the contribution of primary particles is significant only for aggregates of very small size.

As the primary particles size is much smaller compared to the applied laser wavelength, another important piece of information that can be extracted from the static light scattering signal is the cluster fractal dimension, $d_f$. According to the Rayleigh-Debye-Gans (RDG) theory the average structure factor $\langle S(q) \rangle$ scales with q as:

$$\langle S(q) \rangle \propto q^{d_f}, \text{ for } 1/\langle R_g \rangle < q < 1/R_p \qquad (5)$$

Therefore, plotting S(q) vs q in a double logarithmic plot should yield a straight line with slope equal to $d_f$.

Scanning Electron Microscopy—SEM (Zeiss Gemini 1530 with field emission gun operated at 1 kV) was conducted to assess the shape, surface morphology and size of microclusters, as well as to estimate an order of magnitude of the pores size.

The specific surface area was calculated from the Brunauer-Emmett-Teller equation (BET) by analyzing the initial slope of the nitrogen adsorption isotherm obtained through nitrogen sorption measurements (Micromeritics TriStar Series 320). Pore size distribution and corresponding pore volumes were assessed by combining the data obtained through nitrogen sorption and Mercury Intrusion Porosimetry—MIP (Porosimeter 2000). The complete N2 adsorption-desorption cycle was evaluated, especially the desorption isotherm by applying the Barret-Joyner-Halenda (BJH) method for the pore size distribution of small pores (<150 nm). The Hg intrusion isotherm was also evaluated, while the Washburn equation was applied for the pore size distribution of large pores (>20 nm), using a Hg contact angle of 130°, under the assumption of cylindrical pores. All measurements were conducted according to standard operating protocols.

Latex Preparation:

The properties of the primary latex particles, i.e. size, crosslinking degree and functionality, are important to the properties of the final material and can be independently tuned during latex preparation. In this study, two emulsion polymerization procedures were employed, mini-emulsion polymerization and a seeded emulsion polymerization. Both of them provides better control over the particle size with respect to conventional emulsion polymerization. As mini-emulsions are critically stabilized systems, droplet and consequently final polymer particle size depend directly on the surfactant amount with respect to monomer, while using an oil-soluble radical initiator is possible, thus avoiding ionic chain ends.

Details for the synthesis of each of the latexes considered in this work are reported in Table 1. Via a semi-batch protocol a core is first prepared in a miniemulsion batch ("initial core batch" column in Table 1), followed by two starved feeding loops ("1st and 2nd starved feeding loop" columns in Table 1) for growing the two respective outer shells. Thus, control of crosslinking degree along the particle radius and of surface functionality is also possible. The procedure was as follows: The oil phase was prepared by mixing styrene, DVB, HD and AIBN; this was subsequently added to the water phase containing SDS; immediately after ultrasonication (90% amplitude, full cycle, using a Hielscher UP400S ultrasonicator) in an ice bath for a given time, a second aliquot of surfactant was added for post-stabilization. The mini-emulsion thus produced was transferred inside a 3-neck 500 ml round flask, equipped with reflux condenser and magnetic stirrer, degassed and heated to 70° C. When conversion reached ~80%, the two monomeric mixtures corresponding to the two feeding loops were successively fed using a Lamda Vit-Fit programmable syringe pump operated at 0.056 ml/min, while heating was maintained overnight.

TABLE 1

Recipe for primary particles latexes using mini-emulsion polymerization

| | MP11 | | | MP13 | | | MP14 | | | MP16 | | |
|---|---|---|---|---|---|---|---|---|---|---|---|---|
| | | | | | | Batch | | | | | | |
| | Init. | $1^{st}$ | $2^{nd}$ | Init. | $1^{st}$ | $2^{nd}$ | Init. | $1^{st}$ | $2^{nd}$ | Init. | $1^{st}$ | $2^{nd}$ |
| St (g) | 26.2 | 15.8 | 7.2 | 31.6 | 15.8 | 7.2 | 26.2 | 13.1 | 5.18 | 26.2 | 18.2 | 10.4 |
| DVB (g) | 5.8 | 0.20 | 0.16 | 0.40 | 0.20 | 0.16 | 5.8 | 2.90 | 2.18 | 5.8 | 0.23 | 0.23 |
| MCA (g) | — | — | 5.44 | — | — | 5.44 | — | — | 5.44 | — | — | 7.83 |
| HD (g) | 1.28 | — | — | 1.28 | — | — | 1.28 | — | — | 1.28 | — | — |
| AIBN (g) | 0.64 | — | — | 0.64 | — | — | 0.64 | — | — | 0.64 | — | — |
| $H_2O$ (g) | 426 | — | — | 426 | — | — | 426 | — | — | 426 | — | — |
| $SDS_{tot}$ (g) | 0.96 | — | — | 0.96 | — | — | 0.96 | — | — | 3.19 | — | — |
| $SDS_{post}$ (wt. %) | 33 | — | — | 33 | — | — | 33 | — | — | 20 | — | — |
| $t_{sonic}$ (min) | 5 | — | — | 5 | — | — | 5 | — | — | 20 | — | — |

Init.: initial core batch,
$1^{st}$: $1^{st}$ starved feeding loop,
$2^{nd}$: $2^{nd}$ starved feeding loop,
$SDS_{tot}$: total SDS amount applied,
$SDS_{post}$: wt. % of SDS aliquot applied for post-stabilization dissolved in 16 ml $H_2O$,
$t_{sonic}$: ultrasonication time.
Procedure followed described in section "Latex Preparation".

When using seeded emulsion polymerization the primary particle latex was produced in two steps. In the first step a 20% cross-linked core is prepared which is used as a seed in the second step, a seeded emulsion polymerization. There, a 1% cross-linked shell is prepared around the core. Both steps are carried out in semi-batch mode with slow monomer feed in order to achieve a radially more homogeneous cross-linkage than would occur in batch due to the different reactivity of divinylbenzene and styrene [polymer handbook, Brandrup J. et al. (editors), Wiley 1999].

The core particles are produced by semi-batch emulsion polymerization under nitrogen atmosphere. A 4 L Mettler-Toledo LabMax is initially charged with water and surfactant (SDS) according to the recipe reported in Table 2 (initial charge 1, IC1). The temperature is set to 70° C. using the oil heating jacket. In a second flask, an emulsion of styrene, divinylbenzene, water and surfactant (SDS) is prepared according to Table 2 (continuous feed 1, CF1) and kept emulsified using a magnetic stirrer. When the reactor temperature reaches 70° C., aqueous initiator (KPS) solution is injected through a septum into the reactor using a syringe and hypodermic needle according to Table 2 (Initiator solution 1, IS1) and the monomer emulsion is fed at 1.5 mL/min. The reaction progress is monitored with thermogravimetric dry content analysis and dynamic light scattering. The reaction is stopped when reaching a particle size of 105 nm. The shell around the core is prepared with the same procedure, adding the seed latex in the initial charge.

TABLE 2

Exemplary recipe for the production of the precursor core/shell latex using seeded styrene emulsion polymerization. Other monomer/ cross-linker combinations polymerizable using emulsion polymerization (e.g. VBC/DVB, MMA/EGDMA, GMA/EGDMA, VAc/EGDMA) can be polymerized accordingly.

|  | Core Particles | | | Shell | | |
| --- | --- | --- | --- | --- | --- | --- |
|  | IC1 | CF1 | IS1 | IC2 | CF2 | IS2 |
| $H_2O/g$ | 1200.0 | 539.0 | 100.0 | 166.0 |  | 100.0 |
| Styrene/g |  | 573.0 |  |  | 133.0 |  |
| DVB/g |  | 143.0 |  |  | 1.4 |  |
| SDS/g | 2.6 | 12.0 |  |  |  |  |
| KPS/g |  |  | 1.3 |  |  | 2 |
| Seed latex/g |  |  |  | 1600.0 |  |  |
| Diameter/nm |  | 105 (0.016 PDI) | |  | 125 (0.018 PDI) | |

Measurement of CCC:

The critical coagulation concentration was measured for all latexes, in order to identify proper destabilization conditions. An example of the time evolution of the aggregate size measured for various $MgCl_2$ concentrations under quiescent conditions by DLS for the latex MP11 is shown in FIG. 2a. The $MgCl_2$ concentration increases significantly the aggregation rate (RLCA conditions) in the range from 7.63 mM to 31.25 mM, while above 62.5 mM further increase of salt concentration does not affect the aggregation rate (DLCA). By plotting the evolution of initial aggregation rate as a function of salt concentration, the CCC was estimated as shown in FIG. 2b. Actually, all latexes exhibit very comparable CCC values (see Table 3), in line with their very similar $\zeta$-potential values.

TABLE 3

Properties of PS primary particles

| Latex # | DVB (mol. %) | $d_p$ (nm) | $d_{core}$ (nm) | $r_{shell}$ (nm) | $V_\zeta$ (mV) | CCC (mM) | $S_{comp}$ (m²/g) | $x_{dry}$ % |
| --- | --- | --- | --- | --- | --- | --- | --- | --- |
| MP11 | 15/1 | 161 | 139 | 11.0 | −42.3 | 33.0 | 35.3 | 12.0 |
| MP13 | 1/1 | 144 | 119 | 12.5 | −48.4 | 22.5 | 39.5 | 11.7 |
| MP14 | 15/15 | 162 | 141 | 10.5 | −49.1 | 22.5 | 35.1 | 11.4 |
| MP16 | 15/1 | 96 | 75 | 10.5 | −53.2 | 35.0 | 59.9 | 13.3 |

DVB: DVB mol. % in core/$1^{st}$&$2^{nd}$ shell resp.,
$d_p$: final nanoparticle diameter,
$d_{core}$: core diameter,
$r_{shell}$: $1^{st}$&$2^{nd}$ thickness,
$V_\zeta$: $\zeta$-potential,
$S_{comp}$: computed primary particle specific surface area,
$x_{dry}$: final latex dry fraction Latex Swelling:

In the case of the latex produced by the mini-emulsion polymerization swelling was done as follows: A mixture of monomers (15% wt. with respect to the latex dry fraction) containing 20% wt. St, 39% DVB, 40% MCA and 1% AIBN was added dropwise over 20 min into a flat-bottom 30 ml vial containing typically 2.2 g of latex particles (dry basis), under vigorous stirring. The latex was kept under these conditions for another 60 min. Latex produced by the seeded emulsion polymerization was swollen as follows: A mixture of monomers (20% wt. with respect to latex dry fraction) containing 75% wt. of the monomer used to create the particles, 20% wt. of the corresponding cross-linker and 5% wt. AIBN was added at once into a 20% wt. suspension of latex particles. The mixture was kept gently stirred at room temperature for 4 hours.

Aggregation Using Shear DLCA Conditions:

For microcluster preparation the previously swollen latex was diluted down to 1% wt. with water inside a completely filled 150 ml jacketed reactor. To ensure good mixing the reactor was equipped with four paddle impeller and two baffles. Aggregation was induced under defined stirring speed, i.e. shear rate, by two successive gradient salt addition steps, using a Lamda Vit-Fit programmable syringe pump operated at 4.23 ml/min: first 10 ml of 0.5 M $MgCl_2$, followed by 10 ml of 4.9 M $MgCl_2$. A small opening on the reactor lid was used to allow liquid overflow and prevent air from entering the system. The amount of added salt was defined such as to reach a concentration ~15 times above the latex CCC, in order to ensure complete destabilization and incorporation of primary particles into clusters, leading to rapid aggregation. To reach dynamic equilibrium between aggregation and breakage the system was stirred at constant rotation speed for 4 hours.

Aggregation Using Shear RLCA Conditions:

For microcluster preparation the previously swollen latex with the concentration of 23% wt. was diluted down to 14% wt. with deionized water or 0.009 M solution of $MgCl_2$. In the case of salt solution addition its concentration in the final solution was equal to ⅓ of the latex CCC. A value of ⅓ of the CCC was found to work well, significantly destabilizing particles but not making them to aggregate to a noticeable degree during handling. The (meta-)stable latex is then passed through the micro-channel (Homogenizer HC-5000, Microfluidics, USA) to expose the system to very high shear forces, inducing aggregation. Depending on dry content, the extent of electrostatic (de)stabilization and the applied shear forces, the leaving material morphology changes; briefly, more salt, higher shear stress and higher particle fraction lead towards higher aggregation rates and thus gel formation. The exact value of the shear rate depends on the latex and can be evaluated as follows. The preferred product for the next step is a slurry of aggregates with high conversion from primary particles to aggregates: this is best achieved by choosing a dry content that is too low to form a gel spanning the whole system volume at the obtained fractal dimension, e.g. 5%, thus achieving only local gelation to aggregates. This results in a slurry of aggregates with low viscosity, making it easy to handle.

Aggregation Using Stagnant RLCA Conditions:

For comparison purposes a monolith has also been prepared in this work by stagnant reactive gelation. The final salt concentration was kept well below CCC (13 mM) to ensure partial destabilization and therefore rather slow aggregation (see FIG. 2a). In this case, in order to obtain a uniform macroscopic gel the mixing of salt solution with the highly concentrated latex has to be much faster than the subsequent gelation process. Therefore, a 70 mM $MgCl_2$ solution was added dropwise under stirring during ~30 s into a 15 ml flat-bottom vial containing 375 mg of previously swollen latex particles (dry basis), in an amount such as to reach a final gel dry fraction of 10%. The magnetic stirrer was then removed and the latex gelation was left to complete overnight.

The selection of electrolyte type and concentration was based on an optimization, in order to obtain a single-piece, mechanically rigid monolith. Actually, $MgCl_2$ was found to have a smoother effect on the latex gelation than $CaCl_2$, presumably due to the larger hydration number of $Mg^{+2}$. On the other hand, large amounts of monovalent cations (i.e.

Li+, Na+, K+) were required to destabilize the latex, which could result in salt crystals inducing cavities formation. Moreover, the gel dry fraction would be smaller than the targeted 10% if the salt solution concentration was to be retained well below 1 M, so as to avoid improper local mixing effects.

Figure 2:
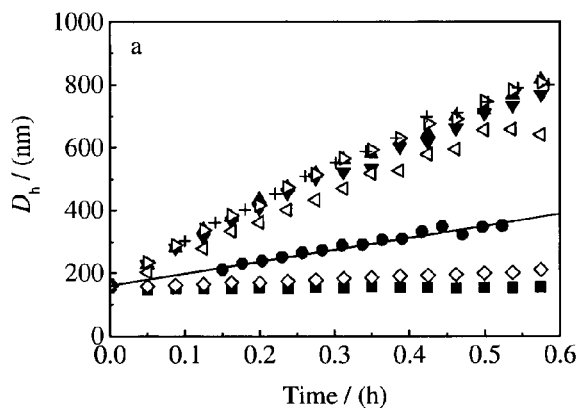
FIG. 2 shows in (a) an example of the aggregation kinetic measured by light scattering under stagnant conditions at different MgCl2 concentrations using primary particles with diameter of 161 nm at solid volume fraction equal to $1.0 \times 10^{-6}$; (■) $c_{MgCl_2}$ =7.63 mM, (◇) $c_{MgCl_2}$=15.63 mM, (●) $c_{MgCl_2}$=18.75 mM, (◁) $c_{MgCl_2}$=31.25 mM, (▲) $c_{MgCl_2}$ =62.5 mM, (▷) $c_{MgCl_2}$=125 mM, (▼) $c_{MgCl_2}$=250 mM, (+) $c_{MgCl_2}$=500 mM; solid line represents linear fit to experimental data with the intercept crossing primary particle diameter at t=0 h; (b) the slope of the linear fit plotted for various salt concentration used to determine the critical coagulation concentration (CCC) of MgCl2 to reach complete destabilization of primary particles
Figure 2:
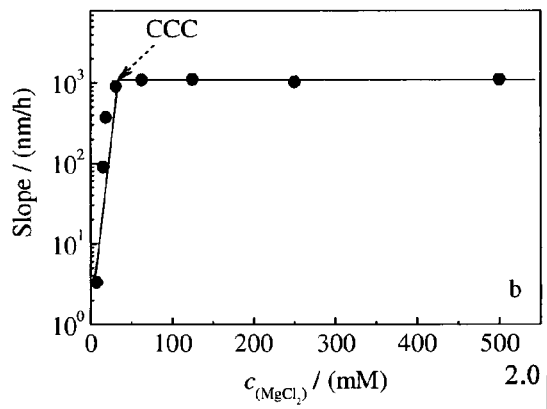

Shear-Ionic Strength Phase Diagram:

The phase diagram characterizes the general behavior of the colloidal system exposed to an elevated level of shear rate (l/s) and/or ionic strength (mol/L). There are two particular points on the boundary of this phase diagram corresponding to no shear rate and no salt (zero ionic strength). In the first case, i.e. zero shear rate, the salt concentration is varied to identify the critical salt concentration required for complete destabilization of the primary particles, above which no further increase of the aggregation rate can be obtain by increasing the salt concentration. This methodology is depicted in FIG. 2 and connected text. The CCC value is system specific and depends on factors influencing the potential barrier of the particles (surface (charge) group type and amount, type of salt or acid/base that is used for destabilization) as well as primary particle size and primary particle properties (material, swelling degree). The theoretical meaning of the CCC is the boundary between static RLCA and static DLCA.

The other crucial point of the phase diagram is the critical shear rate at zero salt, a point where aggregation of primary particles is possible without modification of the potential barrier stabilizing the particles. This point is obtained by applying varying levels of shear rate on the unmodified primary particles (possibly diluted with water, no further chemicals added) and observing above which shear rate primary particle aggregation takes place. This critical shear rate is a function of primary particle size, properties (material, swelling degree) and concentration, type and amount of surface charge groups, type of flow and residence time in the defined apparatus. In our case a homogenizer L30Z from Microfluidics (Newton, Mass., USA) was used.

To summarize applied conditions the phase diagram describing all above mentioned aggregation conditions is presented in FIG. 3 and it was constructed as follows: First, the critical coagulation concentration is determined by a general procedure in which the aggregation kinetics are measured at zero shear with varying salt concentration, as described in FIG. 2. Then, the critical shear rate is determined. Since this is dependent on the primary particle concentration, the shear rate is set to the device maximum and the dry content varied. The more straightforward analysis of fixing a dry content and changing the shear rate could lead us to shear rate values above our device maximum. The gel point was therefore identified by measuring the viscosity of the liquid leaving the microchannel for these different dry contents and looking for its sudden increase, obtaining a dry content value at which our device's maximum shear rate is the critical shear rate (see FIG. 4). It is important to remember that when we change the primary particles the critical shear rate will be different but this procedure is generally applicable.

These two points mark the beginning and end of the phase boundary. Additionally, a third point is placed in the middle to define the curvature of the boundary. For this purpose, we repeat the same experiment using latex with the dry content determined in the step before, but now reduce its colloidal stability by adding salt in such a manner to stay below the critical coagulation concentration. In this experiment the shear rate is systematically reduced starting from the critical shear rate determined earlier (which, due to the design of the experiment, is the device's maximum shear rate, too) and the viscosity of the liquid leaving the micro-channel is measured. Again, the point where a sudden increase of is detected and defined as the critical shear rate for that particular salt concentration and latex dry content. Similar to before, this point would be different for another colloidal system but the concept how to measure it is the same.

Figure 3:
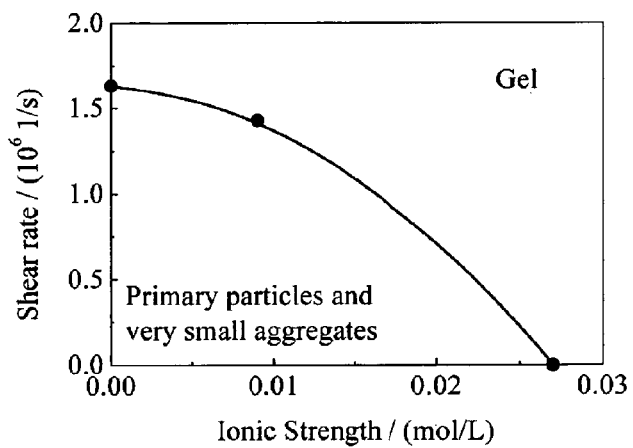
FIG. 3 shows a phase diagram describing the morphology of the material leaving the micro-channel as a function of applied pressure and salt concentration.
Figure 4:
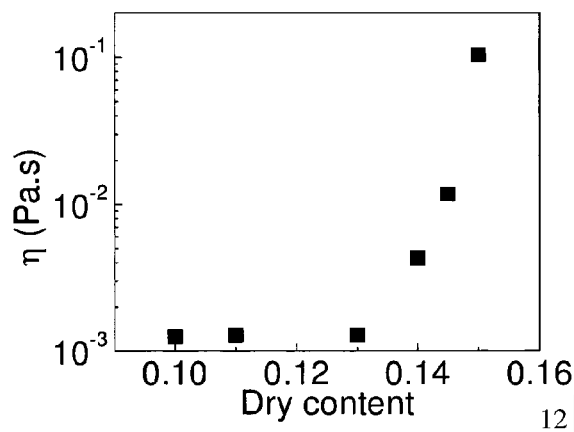
FIG. 4 shows a viscosity of the material leaving the micro-channel at device maximum shear rate. A divergence can be observed at dry contents between 0.13 and 0.14.

Connecting these three points with a quadratic function forms the phase boundary, as depicted in FIG. 3. Below this line no gel formation is observed while at or above this line gelation can be obtained. Parameters of the phase boundary are highly system dependent but can be determined by anyone skilled in the field using above methodology. For this system, the fit is described by the equation $$S=-2.1\times10^9 I^2 - 3.8\times10^6 I + 1.6\times10^6$$

where S is the shear rate (l/s) and I the ionic strength (mol/L).

Stagnant Aggregation:

For comparison purposes a monolith has also been prepared in this work by stagnant reactive gelation. The final salt concentration was kept well below CCC (13 mM) to ensure partial destabilization and therefore rather slow aggregation. In this case, in order to obtain a uniform macroscopic gel the mixing of salt solution with the highly concentrated latex has to be much faster than the subsequent gelation process. Therefore, a 7 0 mM MgCl2 solution was added dropwise under stirring during ~30 s into a 15 ml flat-bottom vial containing 100 mg of previously swollen latex particles (dry basis), in an amount such as to reach a final gel dry fraction of 10%. The magnetic stirrer was then removed and the latex gelation was left to complete overnight.

The selection of electrolyte type and concentration was based on an optimization, in order to obtain a single-piece, mechanically rigid monolith. Actually, MgCl2 was found to have a smoother effect on the latex gelation than CaCl2, presumably due to the larger hydration number of Mg+2. On the other hand, large amounts of monovalent cations (i.e. Li+, Na+, K+) were required to destabilize the latex, which could result in salt crystals inducing cavities formation. Moreover, the gel dry fraction would be smaller than the targeted 10% if the salt solution concentration was to be retained well below 1M, so as to avoid improper local mixing effects.

Post-polymerization and Post-treatment:

Post-polymerization was conducted by keeping the stirred reactor (resp. the gel vial) at 65° C. for 16 h. Afterwards the aqueous layer was decanted (in the case of microparticles following centrifugation at 4600 rpm for 15 min) and the resins were washed 6 times with water and dried slowly at ambient conditions. For subsequent analyses the microclusters were used as such, while the monolith was further ground using a universal mill Oka M20) into micrometer-sized particles for SLS, SEM and N2 sorption characterization, while a few millimeter-sized pieces were reserved for Hg porosimetry (v.i.).

Post-polymerization of the aggregates leaving the micro-channel takes place in a stirred tank at elevated temperature (70° C. over night) applying shear rate orders of magnitude lower compared to that in the microchannel. The product work-up consists of washing the resin with water and ethanol twice; it is then stored in 20% ethanol/water at room temperature. It could be considered to carry out the post-polymerization in a heated tube connected to the microchannel outlet (possibly after dilution using a mixing node), thus making the whole process continuous.

Fluid Flow Characterization:

In order to obtain a quantitative relation between the microclusters size and the hydrodynamic conditions present during cluster synthesis the fluid flow inside the stirred reactor was characterized by Computational Fluid Dynamics (CFD) simulations using the commercial software ANSYS Fluent v12.1. To obtain mesh independent solutions for rotation speeds from 200 to 800 rpm the computational grid used to discretize the stirred vessel contains from 670,000 to 820,000 elements, respectively. Turbulence was modeled by a standard k-ε model, while flow near the wall was modeled by applying a standard wall function. Due to the rather low solid volume fraction (1% wt.), the flow field was calculated using single phase simulation model with density and viscosity values of water at 20° C., equal to 1000 kg/m3 and 1 mPa·s respectively. The average energy dissipated in the system was calculated from the ratio of the power input, P, over the liquid mass, m, according to:

$$\langle \varepsilon_l \rangle = \frac{P}{m} = \frac{\omega \int_A r \times (\tau \cdot dA)}{m} \quad (5)$$

where A is the surface of impeller and shaft, ω is the angular velocity vector (in rps), r is the position vector, τ is the stress tensor, and dA is the differential surface vector. The obtained values of $\langle \varepsilon_l \rangle$ were used to evaluate the average shear rate, $\langle \gamma \rangle$, according to:

$$\langle \gamma \rangle = \mu \sqrt{\frac{\langle \varepsilon_l \rangle}{\nu}} \quad (6)$$

Characterization of Microclusters:

Aggregates composed of fully destabilized rigid primary particles and held together only by van der Waals attractive forces are extremely fragile, exhibiting different steady state sizes when exposed to different shear rates, i.e. stirring speeds. In this regard, aiming to assess the effect of post-polymerization on mechanical stability the produced microclusters were exposed to two different stirring rates. In a first group of experiments, microclusters were prepared at 200 rpm from swollen primary particles of latex MP11 (for characteristics of MP11 see Table 3) without applying post-polymerization. A sample was withdrawn and diluted from $10^{-2}$ w/w to ~$10^{-5}$ w/w so as to ultimately suppress aggregation. Following SLS analysis, these aggregates were stirred inside an identical reactor at 800 rpm until a new steady state was reached and were then reanalyzed by SLS. In a second group of experiments the procedure was repeated according to the same protocol, with the only difference that post-polymerization was carried out after the aggregation at 200 rpm.

Figure 5:
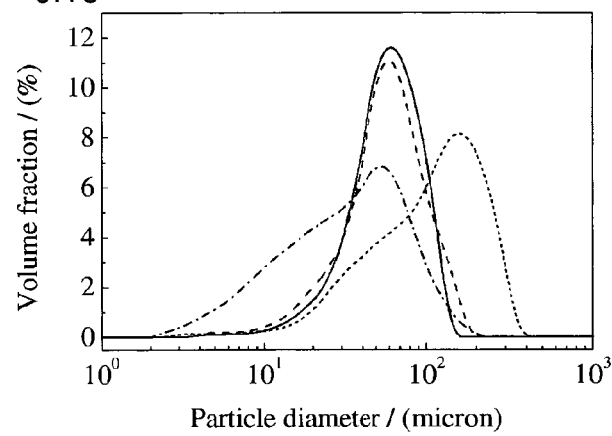
FIG. 5 shows the effect of post-polymerization on the mechanical strength of formed clusters; particle size distribution of microclusters prepared at 200 rpm by aggregation/breakage and stirred at 200 rpm (solid line) and 800 rpm (dashed line) after post polymerization and at 200 rpm (short dashed line) and 800 rpm (dash-dotted line) before post polymerization.

A comparison of the obtained particle size distributions (PSD) by SLS for all four samples is presented in FIG. 5. There is substantial size reduction for the microclusters which did not undergo post-polymerization when the stirring speed is increased from 200 to 800 rpm (see short dashed line vs. dash-dotted line in FIG. 5). On the other hand, post-polymerization does in fact increase substantially the clusters' strength, as clearly indicated by the comparable PSD obtained for both stirring speeds of 200 and 800 rpm (solid and dashed line in FIG. 5). In other words, post-polymerization practically eliminates the dependence of the microclusters' steady-state size on increasing stirring speed. A direct comparison of the absolute sizes and the broadness of the distributions before and after post-polymerization is however difficult (solid vs. short-dashed line in FIG. 5). This is because during the short time needed for sample withdrawal and dilution (<1 min) from the first reactor, the aggregation in the non post-polymerized sample is still on-going. Thus, the different shearing environment causes an observable increase of the cluster sizes and an alteration of their structure before the SLS measurement is realized.

Figure 6:
FIG. 6 shows SEM pictures of formed clusters at two different magnifications (a), (b) using dp=161 nm and stirring speed of 200 rpm; circles indicate rather large throughpores, (c) indicates light scattering measurement results used to measure the internal structure of the aggregates as shown in (a) an (b), wherein the high slope shows that the aggregates are internally very compact.
Figure 6:
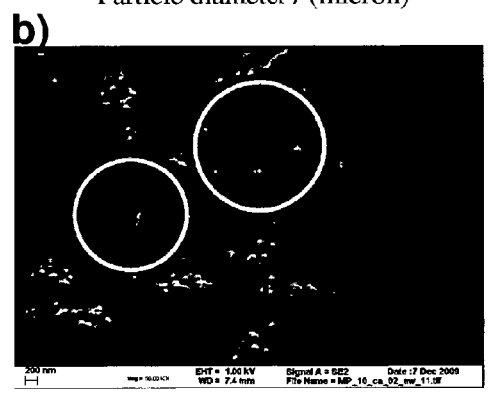
Figure 6:
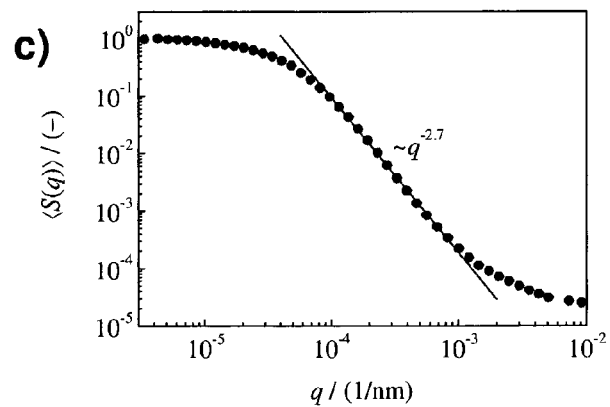

Illustrative SEM images of microclusters prepared with shear-induced aggregation and post-polymerization are presented in FIG. 6a-b. At low magnification (FIG. 6a) the clusters appear to be rather large, irregularly shaped and polydisperse. High magnification (FIG. 6b) clearly reveals compact packing of primary particles on the surface of the formed clusters, with the primary particles visibly interpenetrated, however without having lost their individuality completely. Since the SEM cannot provide information about the internal microcluster structure, further investigations were performed by light scattering. In particular, from the linear region of the double logarithmic plot $\langle S(q) \rangle$ vs. q, such as the one shown in FIG. 6c, the fractal dimension of the microclusters can be estimated. The value of $d_f$ equal to ~2.7 indicates a very compact internal structure, which should arise through the densification mechanisms discussed in the introduction. The $d_f$ value of ~2.7 is considerably larger than the corresponding $d_f$ values for aggregates composed of rigid primary particles produced under stagnant conditions applying DLCA and RLCA namely ~1.8 and ~2.1 respectively, indicating much more open internal structures. Yet, the $d_f$ obtained for our microclusters is in good agreement and only slightly larger than the corresponding value for aggregates produced under shear from fully destabilized rigid primary particles, namely ~2.6.

Figure 7:
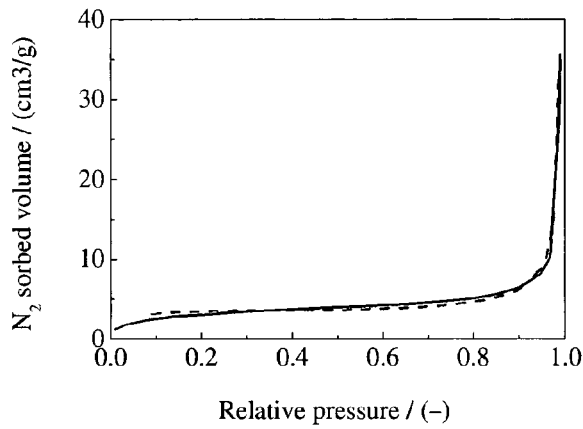
FIG. 7 shows indicative nitrogen adsorption (solid line)-desorption (dashed line) cycle.

Upon visual observation the produced microclusters appear opaque and white, an indication that they are porous with internal agglomerates larger than 200 nm. SEM reveals numerous very large throughpores with diameters of several hundreds of nanometers (see white circles in FIG. 6b), despite the compact internal structure. Based on these preliminary observations additional analyses of specific surface area and pore size distribution were carried out by nitrogen sorption and mercury intrusion porosimetry. An illustrative N2 adsorption-desorption cycle is presented in FIG. 7, which is of isotherm type II according to IUPAC. The absence of hysteresis denotes no mesoporous condensation and therefore very large pores. Furthermore, the asymptotic increase of the sorbed N2 volume at relative pressures approaching unity indicates significant population of macropores. The rather small adsorbed volumes (<5 cm3/g) at low relative pressures indicate absence of micropores. The relatively small BET surface areas measured for all samples, in the order of tens m2/g (see Table 4), further suggest negligible portion of small pores. It is well-known that for pores above 50 nm the reliability of pore size distributions from N2 sorption is limited. Therefore Hg porosimetry was the method of choice to investigate the pore size distribution of our microclusters.

TABLE 4

Effect of primary particle properties and rotation speed on the produced resin properties.

| Latex # | DVB (mol %) | Resin type | Rotation speed (rpm) | $\langle R_g \rangle$ (μm) | $d_f$ (—) | $S_{BET}$ (m²/g) | $S_{Hg}$ (m²/g) | ε (—) |
|---|---|---|---|---|---|---|---|---|
| MP11 | 15/1 | μ-c | 200 | 40 | 2.7 | 11.2 | 9.7 | 0.70 |
| MP13 | 1/1 | μ-c | 200 | 85 | 3.0 | 7.5 | 7.1 | 0.48 |
| MP14 | 15/15 | μ-c | 200 | 40 | 2.3 | 13.1 | 12.3 | 0.66 |
| MP16 | 15/1 | μ-c | 200 | 53 | 2.85 | 30.0 | 35.2 | 0.55 |
| MP11 | 15/1 | mon | 0 | — | 1.9 | 12.6 | 13.4 | 0.69 |
| MP11 | 15/1 | μ-c | 200 | 40 | 2.7 | 11.2 | 9.7 | 0.70 |
| MP11 | 15/1 | μ-c | 400 | 22 | 2.7 | 14.1 | 15.0 | 0.61 |
| MP11 | 15/1 | μ-c | 800 | 16 | 2.7 | 16.7 | 22.9 | 0.60 |

μ-c: microclusters,
mon.: monolith

Figure 8:
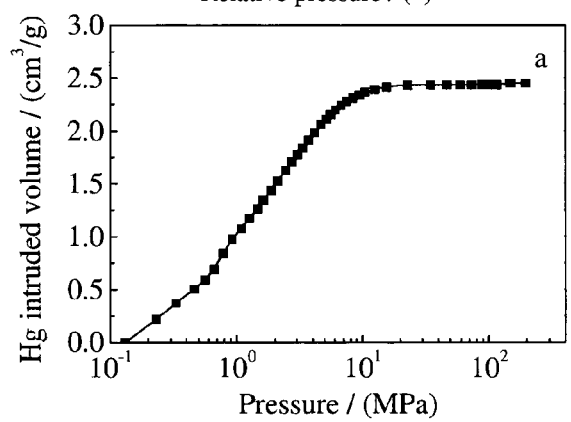
FIG. 8 shows mercury intrusion in clusters composed of primary particles with diameter 161 nm (200 rpm) a: intrusion isotherm, b: differential pore size distribution, c: natural logarithmic differential pore size distribution.
Figure 8:
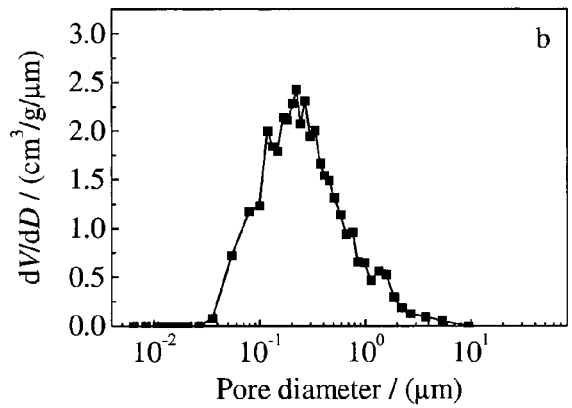
Figure 8:
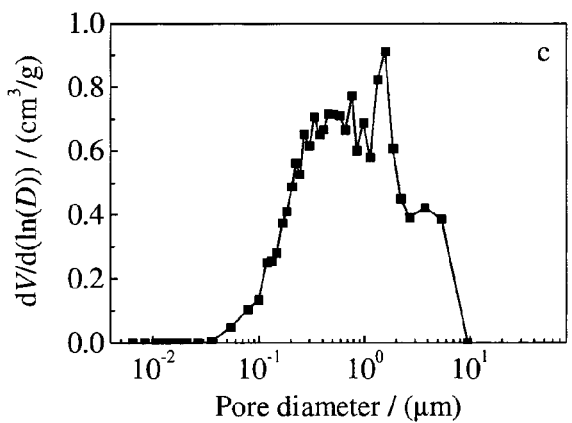

An example of results obtained from Hg porosimetry is presented in FIG. 8a-c. The Hg intruded volume increases over a broad range of applied pressures, until a plateau is reached around 10 MPa extending to approximately 60 MPa. An abrupt increase of intruded volume takes place around 80 MPa, which indicates deformation or collapse of the copolymer matrix. Hence in the calculations for porosity and specific surface area (Table 4), as well as for plotting the pore size distributions for all samples, intruded volumes corresponding to pores smaller than 20 nm, i.e. applied pressures higher than 60 MPa, were neglected. All Hg intrusion isotherms are plotted as received. The onset of the intrusion isotherm was not always followed by a clear intermediate plateau before finally leveling off at high pressures, as for example in FIG. 8a, indicating that Hg intrusion inside the particles was taking place simultaneously with filling of the inter-particle voids. The problem of inter-particle volume is treated in the literature by ignoring volumes corresponding to pore sizes above a certain minimum, provided pores are small enough or by employing a nonporous reference sample. Following the latter approach the intruded volume of nonporous ceramic microparticles of sizes comparable to our samples was subtracted from the intruded volumes of our samples to eliminate its effect on the measured porosities, surface areas and pore sizes. The pore size distributions obtained are plotted in FIGS. 8b and c as dV/dD and dV/d(ln D), respectively. The difference between the two distributions is that when using the logarithmic diameter (plot c) the larger pores are weighted more and therefore such plots are more commonly used for macroporous materials. The pore size distribution is apparently broad, with a weak maximum at 1.6 μm, characterized by the absence of pores smaller than a few tenths of nanometers and the presence of unusually large pores for this kind of resins, reaching sizes of several micrometers. This gives also rise to an unusually high intraparticle porosity of 70% and to small surface area (~10 m2/g), confirming our initial expectations from SEM and N2 sorption analyses (see Table 4).

The generally small discrepancies between the surface area values from BET and Hg intrusion porosimetry are most probably due to the assumption of cylindrical pores used in Hg porosimetry, which is obviously not very accurate for the irregularly shaped macropores of colloidal aggregates. The initial surface area of the primary particles (latex MP11 Table 1) is reduced for the produced microclusters by 68%, from 35 m2/g down to 11 m2/g, a fact suggesting that all the four mechanisms of densification mentioned above are operative. It is also worth to note that despite the clusters being highly porous, they are mechanically robust up to pressures of about 60 MPa (see FIG. 8a).

It is also worth to mention that chromatographic columns were packed with these microclusters and were examined by ISEC. No exclusion up to a molecular probe diameter of ~120 nm (the largest probe used) was observed, a result expectable in light of the vary large pores revealed by Hg porosimetry. Moreover, the corresponding chromatographic peaks appear rather symmetric, with asymmetry factors varying between 1.27 and 1.32 for different probes and having an average of 1.30. Such values are considered fairly low and were actually independent of the probe size. This observation, together with the fact that column efficiency was found to be independent of the flow rate indicate good mass transfer characteristics inside our microclusters, which are probably associated with good pore connectivity.

Effect of Primary Particle Properties:

The characteristics of the four latexes considered in this work are reported in Table 3. All latexes had the same surface functionality (~40 mol. % MCA), similar dry fraction ~12 wt. % and high colloidal stability, indicated by comparable ζ-potential values above 1-40 mV1. The crosslinking degree is uniform along the whole particle radius for latexes MP13 and MP14 and equal to 1 and 15 mol. % respectively. On the other hand, latexes MP11 and MP16 exhibit both a 15% crosslinked core and a 1% crosslinked shell of about 11 nm. The MP16 particles are significantly smaller, namely 96 nm in diameter, as opposed to the other three latexes, whose particle diameter is in between 144 and 162 nm. The purpose of using these latexes as starting materials was to investigate the effect of primary particle size and crosslinking degree on the characteristics of the final material. Effect of crosslinking degree:

The glass transition temperature of a polymer network depends not only on the solvent it may contain, but also on its crosslinking degree. Therefore, particles that are swollen with the same amount of monomer but have different crosslinking densities behave differently during aggregation and post-polymerization, owing to the different flexibility of their polymer chains. The less crosslinked a particle is, the more is softened by monomer swelling and hence the more prone it is to coalescence during aggregation. Moreover, clusters comprising particles with less crosslinked, thus more mobile chains, rearrange easier during post-polymerization. The opposite effects are present with highly crosslinked, and therefore, more rigid particles. It also follows that after post-polymerization the higher the crosslinking degree, the better the resistance of the final resins' network to "good" organic solvents will be.

Figure 9:
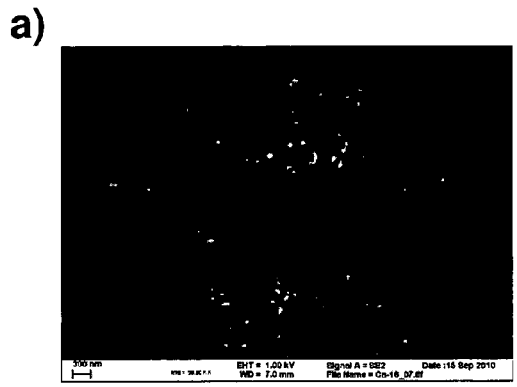
FIG. 9 shows indicative SEM pictures of clusters obtained from primary particles containing (a) 1% DVB and (b) 15% DVB.
Figure 9:
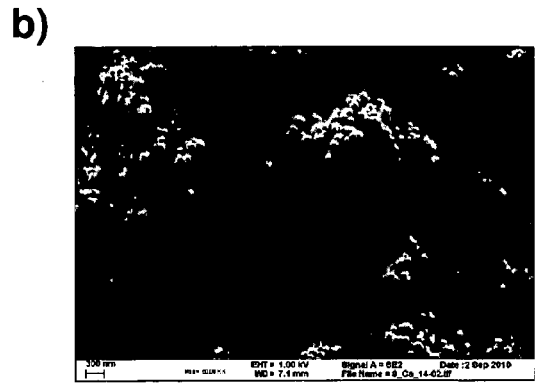
Figure 10:
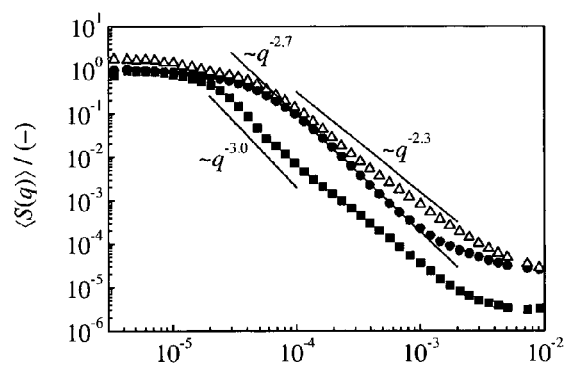
FIG. 10 shows the effect of primary particle DVB content on the size and internal structure of formed clusters; (●) core-shell primary particles with DVB content of 15% in core and 1% in shell, (■) primary particles with DVB content of 1%, (Δ) primary particles with DVB content of 15%.

The effect of primary particle crosslinking was investigated by using latexes MP11, MP13 and MP14 as starting materials (see Table 3). Upon examination by SEM of the microclusters produced from 1% crosslinked latex, their constituting primary particles appear substantially fused together and barely identifiable (see FIG. 9a). Conversely, in the microclusters produced from 15% crosslinked latex the primary particles are apparently less interpenetrated and retain their individuality to a large extent (see FIG. 9b). In microclusters produced from the latex where only the core contained 15% DVB, there is clearly interparticle fusion due to the presence of the lowly crosslinked shell (FIG. 6b). These structural observations from SEM pictures are confirmed by the corresponding surface areas (see Table 4), which are increasing with increasing DVB content, as well as by the fractal dimensions, which are decreasing from 3.0 for 1% crosslinked particles, to 2.7 for core-shell particles and further down to 2.3 for 15% crosslinking (see FIG. 10). The change in slope for large wave vectors q on the structure factor plot for 1% crosslinking (solid squares in FIG. 10) may be attributed to relatively open structures which result from the ductile rupture of the clusters, while still in softened state, under the presence of shear. In fact, regions of different refractive index observable as bright or whitened zones on SEM pictures (see FIG. 9a) are indicative of extensive plastic deformation upon fracture of rubbery materials. Furthermore, owing to the more extensive interpenetration between 1% crosslinked primary particles, the resulting microclusters have larger fracture toughness and they are consequently able to withstand higher stress and grow larger in size (see Table 4).

Figure 11:
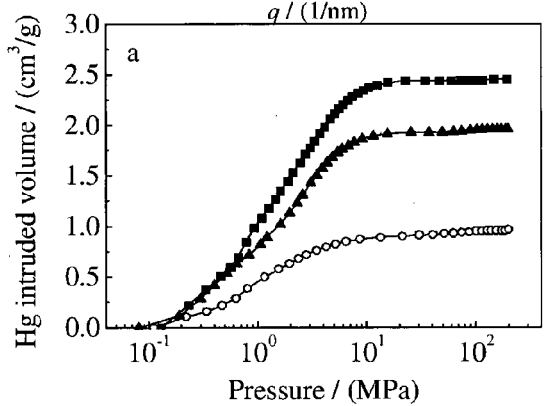
FIG. 11 shows a comparison of intrusion of mercury into clusters composed of primary particles with DVB content of 15% in core and 1% in shell (■), 15% DVB (▲), and 1% DVB (○) prepared at stirring speed of 200 rpm. Comparable diameter of primary particles of about 160 nm was used in all experiments; a: intrusion isotherm, b: natural logarithmic differential pore size distribution.
Figure 11:
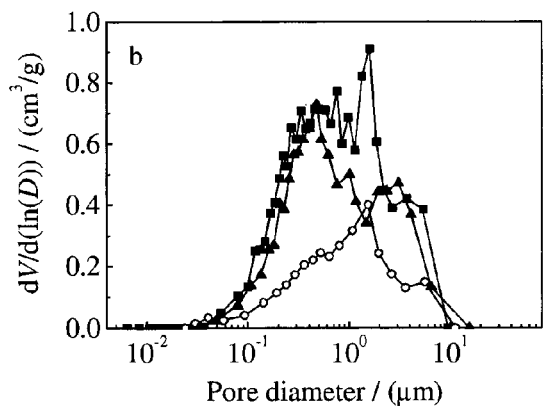

In line with the observations from SEM, SLS, and BET, the porosity measured by Hg intrusion for the microclusters from 1% crosslinked particles is significantly smaller than the corresponding porosities for 15% crosslinked and core-shell particles (see Table 4), as indicated by the plateau height of the intrusion curves in FIG. 11a. The span of the extracted pore size distribution is similarly broad for all three crosslinking degrees, yet it appears that for low crosslinking the distribution maximum is around 1.5 µm, while for low crosslinking is about 500 nm (FIG. 11b). These results indicate that lowly crosslinked primary particles actually coalesce and rearrange to a greater extent during aggregation, breakage, and post-polymerization, so that the resulting fractal structures are more compact and in overall less porous. Through the better rearrangement of the constituting units of a porous structure its pore size distribution will be narrower, which is the case if one considers the appearance of the maximum around 1.5 µm. The fraction of small pores present in such compact clusters is also smaller, presumably due to the more efficient elimination of the relatively small interparticle voids, as opposed to clusters from highly crosslinked particles where such voids prevail. Consequently, mass transport inside microclusters produced from 1% crosslinked particles appears to be even better than in microclusters from 15% crosslinked and core-shell particles, on the basis of the excellent values from ISEC measurements.

Figure 12:
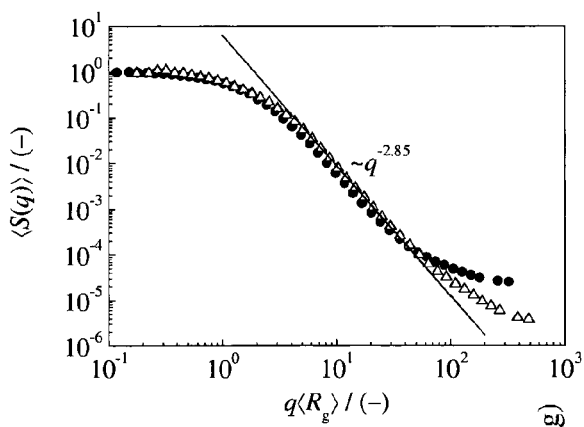
FIG. 12 shows the effect of primary particles size on internal cluster structure measured at stirring speed of 200 rpm; (●) $d_p$=161 nm, (Δ) $d_p$=95 nm; line indicates power law scaling of S(q) vs q⟨$R_g$⟩ (fractal dimension), for this case around 2.85.

Effect of Primary Particle Size:

The effect of primary particle size was investigated using latexes MP11 and MP16 as starting materials. The MP16 overall particle diameter is 96 with respect to 161 nm for MP11, while the rest latex properties, including the lowly crosslinked shell thickness of about 11 nm, as well as preparation procedures were the same (Table 4). The internal cluster morphology from SEM imaging appears similar to the one of clusters from MP11 produced at 200 rpm, which can be explained by the core-shell primary particle type. However, since the relative amount of lowly crosslinked material per particle is 52 vol. % for MP16 latex with respect to 35% for MP11, the relative particle interpenetration for MP16 latex is expected to be larger and the resulting cluster void fraction smaller. Indeed, the $d_f$ value measured by SLS increases to 2.85 (see FIG. 12) and the porosity from Hg intrusion decreases to 0.55 (see Table 4), as opposed to 2.7 and 0.70, respectively, obtained for microclusters generated from larger primary particles. Since the growing clusters are more compact, they are, similarly with those generated by lowly crosslinked particles, able to withstand higher shear rate and ultimately reach larger sizes, namely 53 µm with respect to 40 µm.

Figure 13:
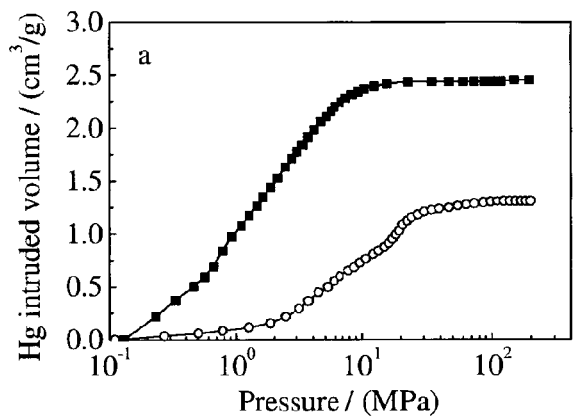
FIG. 13 shows a comparison of intrusion of mercury on cluster composed of primary particles with diameter 161 nm (■) and 95 nm (○) at stirring speed of 200 rpm; a: intrusion isotherm, b: natural logarithmic differential pore size distribution.
Figure 13:
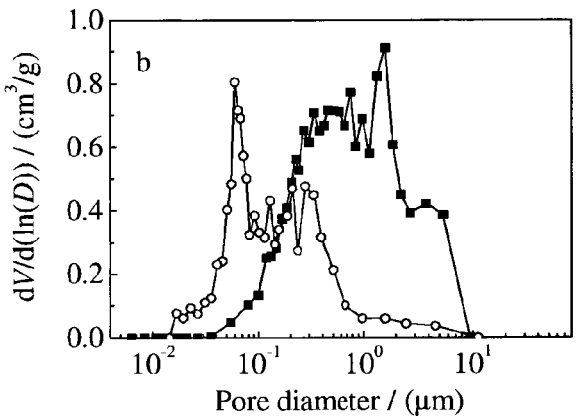

Despite their lower porosity, the specific surface area of clusters produced from smaller primary particles is still approximately 3 times larger compared to the microclusters produced from larger particles (see Table 4). Moreover, from the pore size distribution of FIG. 13 it is evident that, contrary to the microclusters composed of large primary particles, the very large pores between 1 and 10 µm are to a big extent absent. Actually, the distribution has shifted to smaller pore sizes by roughly 1 order of magnitude and is clearly skewed towards its left part, exhibiting a very clear maximum at 60 nm. The primary particle size thus emerges as a key and definitively tunable parameter for controlling the pore sizes of our resins.

Figure 14:
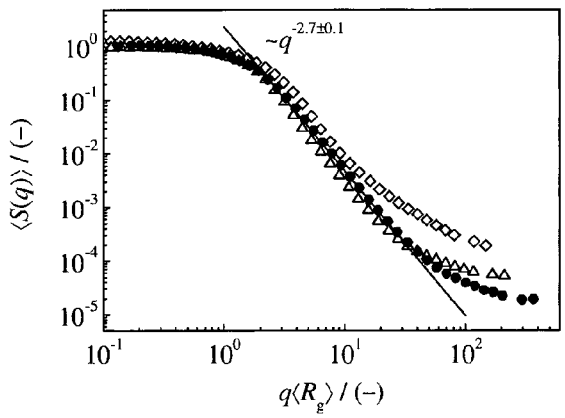
FIG. 14 shows the effect of rotation speed on the internal structure of formed clusters. (●) 200 rpm, (Δ) 400 rpm, (◇) 800 rpm; line indicates power law scaling used to determine cluster fractal dimension which for this was equal to 2.7±0.1

Effect of Operating Parameters—Shear Rate:

The effect of shear rate was investigated by running the aggregation, breakage, and post-polymerization experiments of swollen MP11 latex at different impeller rotation speeds, namely 200, 400 and 800 rpm. With increasing stirring speed, i.e. shear rate, the aggregate size is obviously decreasing (see Table 4 and FIG. 15). However, the internal cluster morphology appears similar for all three rotation speeds, with $d_f$ values about 2.7, essentially unaffected by the change in shear rate (see FIG. 14).

TABLE 5

Summary of the operating conditions in stirred vessel used during aggregation

| Rotation speed (rpm) | Re (—) | Po (—) | $\langle \varepsilon_l \rangle$ (m²/s³) | $\langle \gamma \rangle$ (1/s) |
| --- | --- | --- | --- | --- |
| 200 | 8,076 | 1.65 | 0.132 | 358 |
| 400 | 16,152 | 1.45 | 0.923 | 946 |
| 800 | 32,304 | 1.43 | 7.282 | 2,657 |

Figure 15:
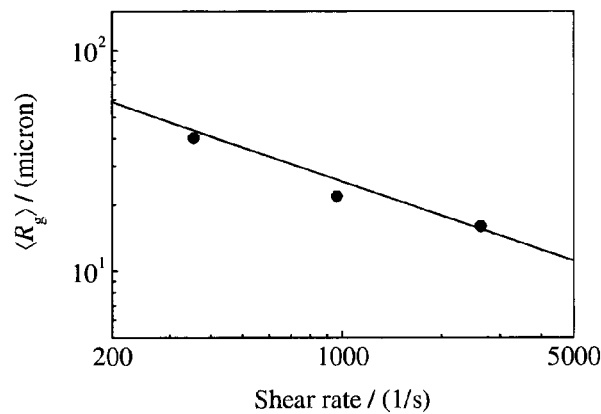
FIG. 15 shows the scaling of cluster size as a function of the applied volume-average shear rate in stirred vessel; all experiments performed with latex MP11 (see also tables)

A correlation of the microclusters size with the applied volume averaged shear rate evaluated by CFD simulations (see Table 5) is presented in FIG. 15. The solid straight line represents the theoretical scaling for the steady-state cluster size $\langle R_g \rangle$ evaluated for $d_f$=2.7. From a practical viewpoint this is very useful as, for given latex, once the cluster size corresponding to certain shear rate is known the sizes for all other shear rates may be predicted.

Figure 16:
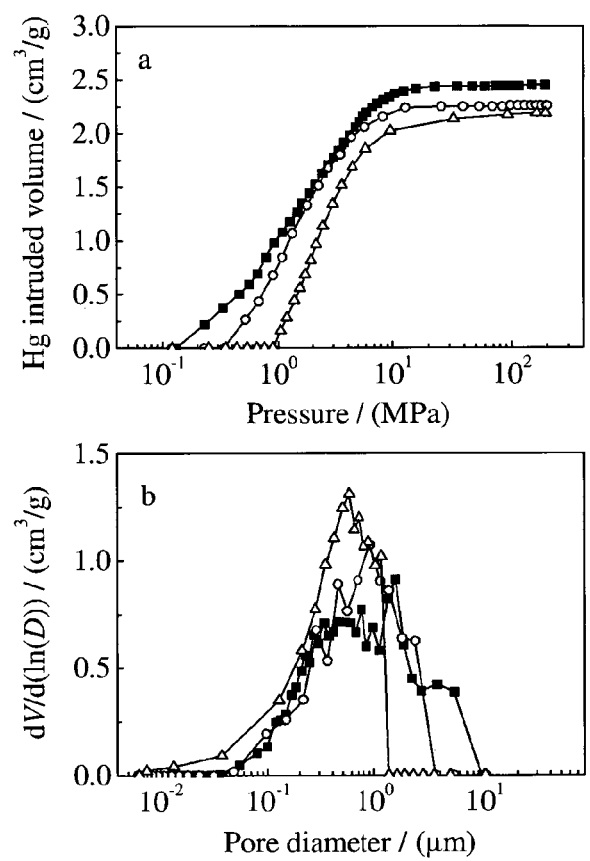
FIG. 16 shows a comparison of intrusion of mercury into cluster prepared under different stirring speeds: (■) 200 rpm, (○) 400 rpm, and (▲) 800 rpm; a: intrusion isotherm, b: natural logarithmic differential pore size distribution.

The void volume fraction of a fractal aggregate decreases when its size decreases. As a matter of fact, the porosity measured is smaller for the smaller clusters prepared at higher rotation speeds (see c values on Table 4 and plateau height of the Hg intrusion isotherms on FIG. 16a). Similarly to the case of microclusters originating from smaller primary particles, the surface areas are increasing with increasing shear rate despite the porosity decrease (see Table 4). This is presumably due to the presence of smaller pores, evidenced by a systematic shift of the pore size distributions to the left (see FIG. 16b). At higher shear rates the recombining cluster fragments that build up the final microclusters are certainly smaller, therefore the resulting pores are again smaller. The applied shear rate is consequently one more parameter for tuning the final pore sizes. Last, owing most probably to the increased fraction of smaller pores, the peak asymmetry factors for clusters produced at 800 rpm are also larger, yet still acceptable, indicating somewhat impaired mass transfer.

Figure 17:
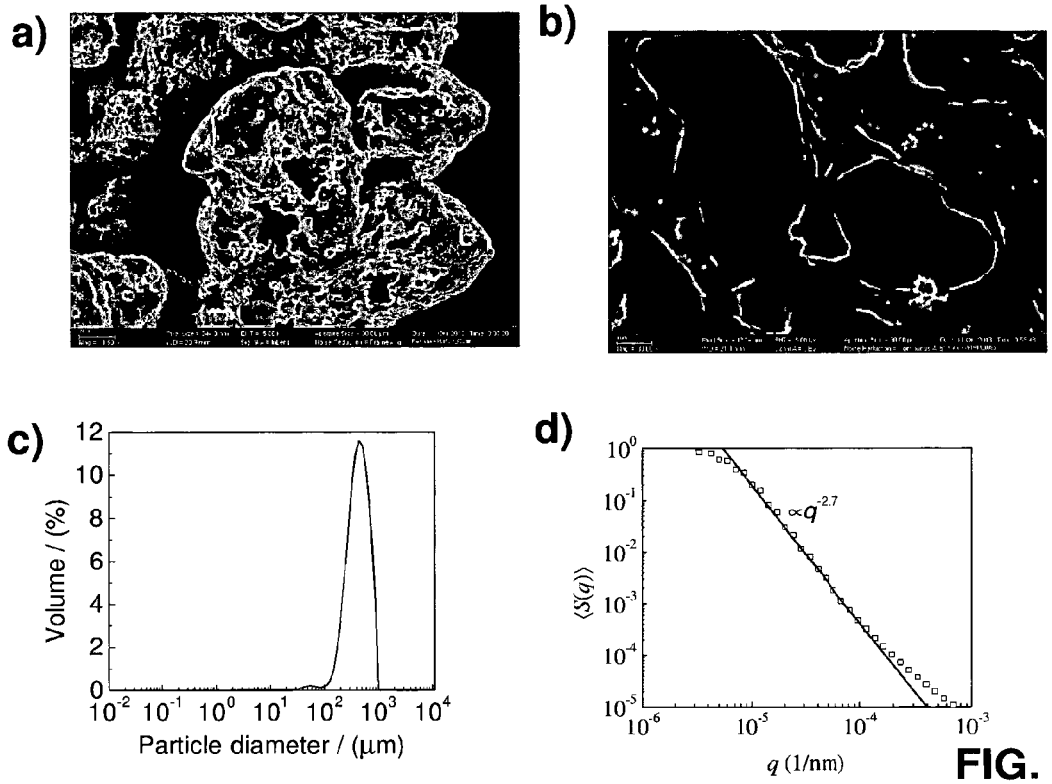
FIG. 17 a) and b) show SEM pictures of polyvinylacetate micro-clusters produced in a stirred tank under DLCA/shear conditions. One can identify the large pores, and can barely identify the strongly fused latex particles used in their production. c) shows a particle size distribution of these clusters; a shoulder at low diameters shows the presence of a small population of intermediate aggregates, however absence of primary particles. d) shows the structure factor ⟨S(q)⟩ as a function of the scattering vector q. As can be seen data over a large size range follow a power law scaling (solid line) with fractal dimension $d_f$=2.7

Effect of Monomer Type:

Following same procedure as describe above μ-clusters of polyvinylacetate (PVAc) nanoparticles were prepared. PVAc has a glass transition temperature of 33° C. (Lovell P. A. and El-Aasser, M. S. (Editors), 1997, Emulsion Polymerization and Emulsion Polymers, Wiley, Chichester, West Sussex, England) and is thus expected to result in particles that are rigid at room temperature. However, during post-polymerization, the temperature rises above $T_G$, plasticizing the particles and making them fuse together. The primary particle latex was prepared in batch emulsion polymerization at 10 wt. % solid content, using 1 wt. % SDS per monomer and 0.1 wt. % KPS in water. The reaction was carried out at 70° C. for five hours. The resulting particles had a diameter of 75 nm with PDI of 0.079 and the CCC was determined to be 37 mM NaCl. These particles were subsequently swollen in 20 wt. % of a mixture of VAc/AIBN 95/5 for four hours and then aggregated in a stirred tank under DLCA conditions. For this purpose, the swollen latex was charged into the reactor to obtain a final solid content of 1.5 wt. %. This suspension was stirred at 600 rpm. Aggregation was induced by charging 26 mL of 2 M NaCl into the reactor and after 4 hours of aggregation and breakage, the reactor temperature was raised to 70° C. for another 4 hours, after which stirring and heating were switched off. The resulting material was then cleaned with water. The particles were characterized using static light scattering, showing an average cluster size of 450 μm with a fractal dimension $d_f$=2.7 (FIG. 17a, b). Scanning electron microscopy confirm the strong particle coalescence while still maintaining large, interconnected pores with size ranging approximately from 1 to 10 microns (FIG. 17c, d). This is in good agreement with microclusters discusses above clearly confirming versatility of the proposed method.

Another example for the modularity of this process is the usage of vinylbenzyl chloride as a pre-functional monomer. Due to the higher cost of this monomer than styrene, only a thin shell of VBC was prepared around the styrene-based latex described in Table 2, increasing the particle diameter from 125 to 135 nm. Except for swelling with VBC/DVB/AIBN (75/20/5), the particles were treated exactly like their pure styrene counter-part, producing practically identical aggregates. However, these aggregates now have 180 μmol/g (determined via ion chromatography) of chloride on their surface. It is commonly known and widely published (e.g. Krajnc et al., Organic Letters 2002, 4, 15, 2497 or Subramonian, Reactive & Functional Polymers, 1996, 29, 129) that this excellent leaving group can be used as precursor for a large number of functionalizations.

Figure 18:
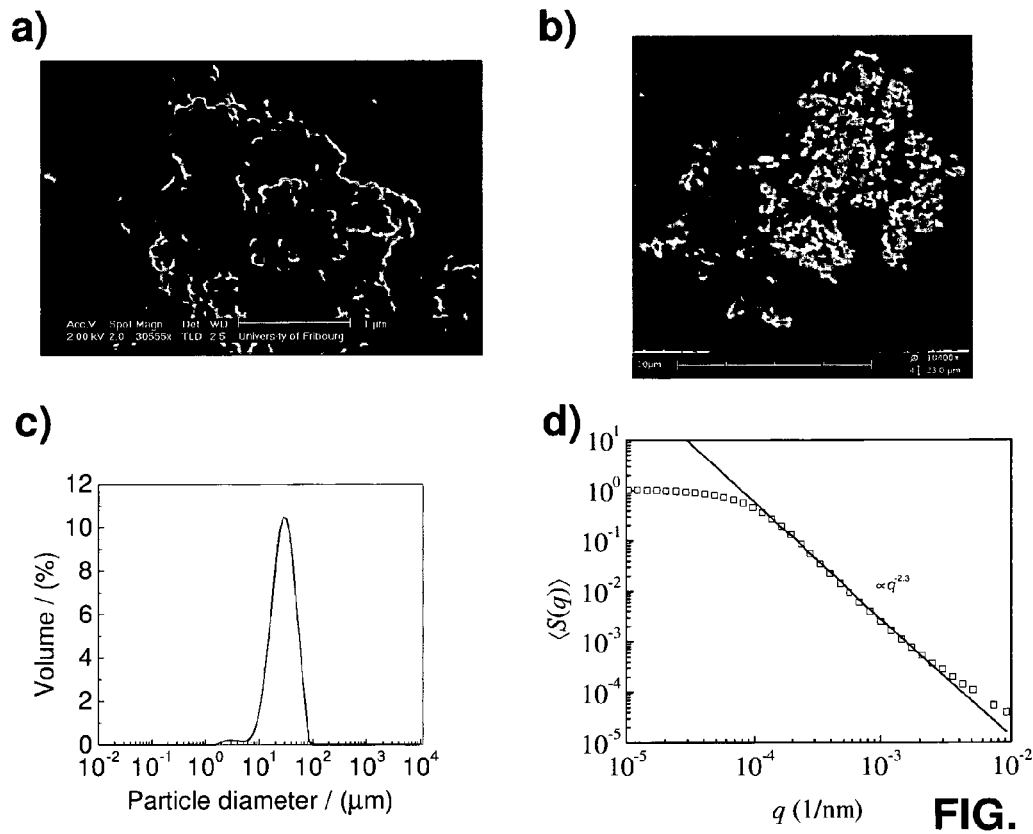
FIG. 18 a) and b) show SEM pictures of micro-clusters produced in the micro-channel under RLCA/shear conditions. One can identify the large pores, and can still differentiate between the slightly sintered latex particles used in their production; c) shows a particle size distribution of these clusters; a shoulder at low diameters shows the presence of a small population of intermediate aggregates, however absence of primary particles. d) shows the structure factor ⟨S(q)⟩ as a function of the scattering vector q. As can be seen data over a large size range follow a power law scaling (solid line) with fractal dimension $d_f$=2.3
Figure 19:
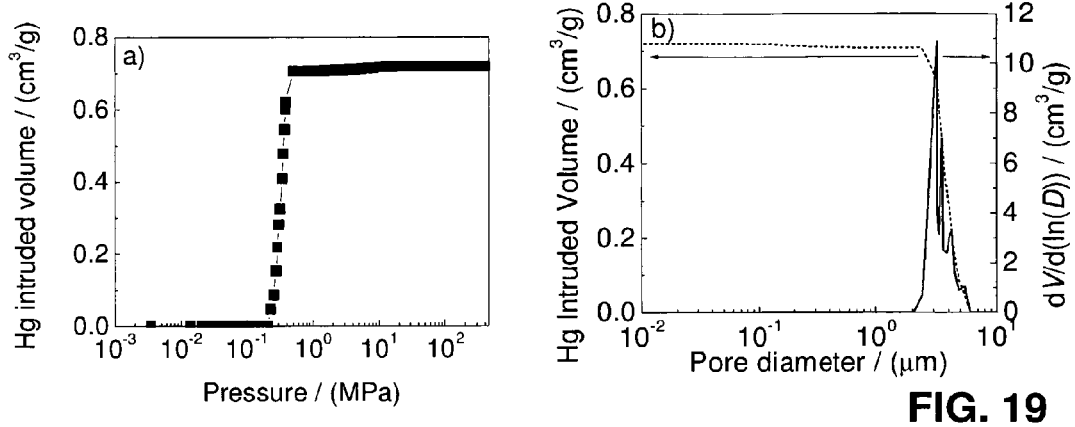
FIG. 19 shows the mercury porosimetry results of a material prepared in the micro-channel. In figure a) is plotted the intruded volume of mercury as a function of applied pressure. In figure b), this is transferred to pore sizes assuming cylindrical pores and the log-differential pore size distribution is calculated FIG. 20 (upper) shows SEM pictures of a monolith, the circle indicates rather large throughpores, (lower) shows a comparison of internal structure of (Δ) monolith prepared by reactive gelation (RLCA conditions) and (●) microclusters prepared by aggregation/breakage and post-polymerization (DLCA under shear)

Aggregates Produced Under Shear RLCA Conditions:

A first impression of the material can be obtained from the SEM pictures in FIG. 18a, b. As can be seen, the aggregates appear macro-porous at low magnification, while at high magnification one can still clearly identify the now slightly fused primary particles the aggregates are formed from. The Brunauer-Emmett-Teller (BET) equation was used to estimate the total surface area to 25.6±0.2 m$^2$/g from nitrogen adsorption/desorption cycles. Static light scattering (SLS) was used to characterize the particle size of the aggregates and the weight scaling law they obey. They were found to be on average 31 μm in diameter (with a small fraction of sub-10-micron particles, see FIG. 18c) and following a power law scaling with a fractal dimension $d_f$=2.3 over a wide range of sizes (FIG. 18d). Mercury intrusion porosimetry was used to assess the support's pore size distribution before latex decoration, assuming cylindrical pores (FIG. 19), exhibiting very large, narrowly distributed pore diameters.

Monolith from Reactive Gelation:

The study on the synthesis of macroporous particulate resins via aggregation, breakage, and post-polymerization would not be complete without a comparison between these microclusters and a monolith from stagnant reactive gelation, since our approach relies to a large extent to procedures adopted therefrom. Such a monolith was prepared by aggregating the same swollen primary particles (MP11) under RLCA conditions, to obtain a single, cluster-spanned network, i.e. colloidal gel, which was subsequently post-polymerized.

Figure 20:
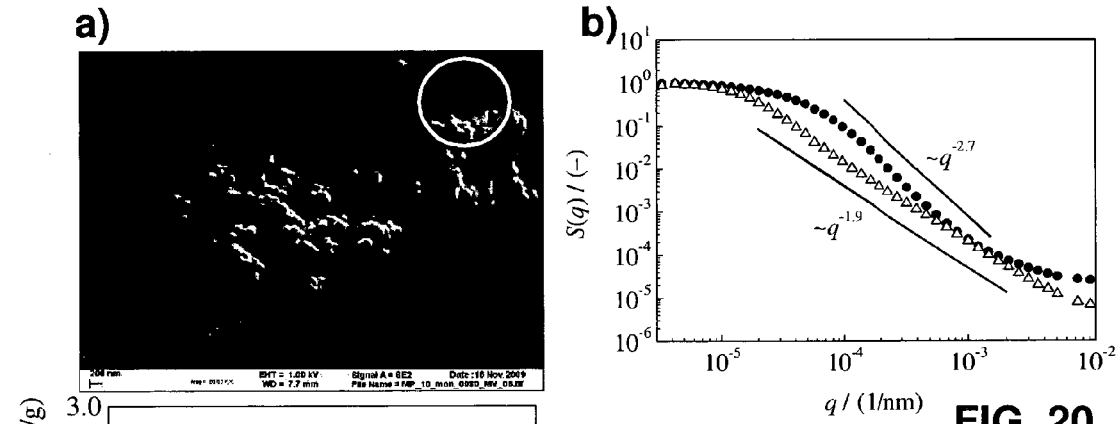

Imaging by SEM does not signify any substantial difference between monolithic (FIG. 20a) and particulate (FIG. 6) resins. However, SLS reveals a much smaller fractal dimension for the monolith, namely 1.9 (see FIG. 20b), indicating a very open internal structure. This low value is substantially smaller than the corresponding $d_f$=2.7 for our microclusters (FIG. 20b) and is consistent with $d_f$ around 2 for rigid primary particles produced under stagnant RLCA. The fact that the colloidal gel and the subsequent monolith are uniform macroscopic objects makes it possible to quantify the compactification associated with post-polymerization. Actually, a remarkable volume shrinkage in the order of 55%, radial as well as axial, takes place during the transition from gel to a rigid monolith. This suggests that apart from the unavoidable shrinkage due to the polymerization itself, coalescence, as well as surface-free energy-induced rearrangement are most probably operative to a significant extent. Therefore, it is also reasonable to presume that post-polymerization of microclusters is similarly inducing certain macroscopic shrinkage.

Figure 21:
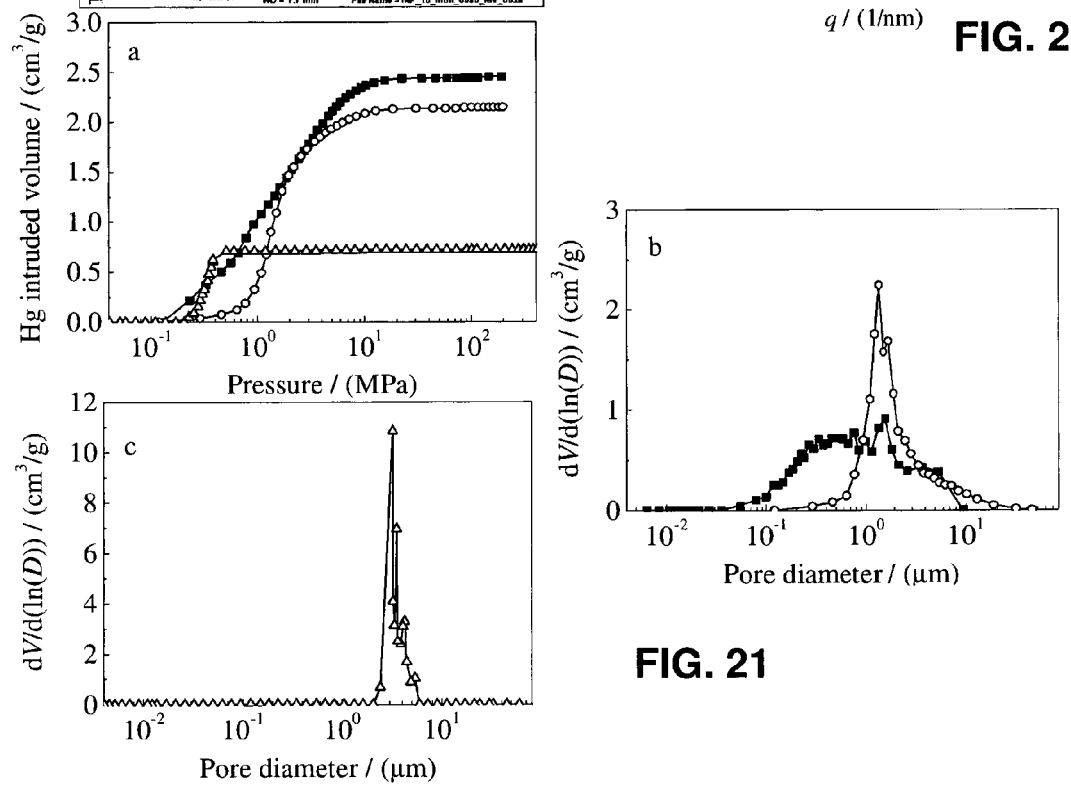
FIG. 21 shows a comparison of mercury intrusion volume into (○) monolith prepared by reactive gelation under stagnant conditions (stagnant RLCA conditions), (■) microclusters prepared by aggregation/breakage and post-polymerization using DLCA under shear conditions, (▲) microclusters prepared by aggregation and post-polymerization using RLCA under shear conditions (a); panel (b) shows comparison of the pore size distribution evaluated from mercury porosimetry for stagnant RLCA (○) and DLCA under shear (■), panel (c) shows the pore size distribution evaluated from mercury porosimetry for shear RLCA (Δ)

The specific surface area and porosity of the monolith are comparable to the corresponding values for the microclusters with rather narrow the pore size distribution with a very pronounced peak maximum around 1.3 μm (see FIG. 21b). This is likely to be due to inherent differences between the two pore-generation mechanisms. In fact, a narrower pore size distribution is associated with better ordering inside the porous structure. This should actually hold for our monolith since a colloidal gel prepared under RLCA conditions is a self-similar object. Conversely when cluster breakage dominates over aggregation, owing to the multiple recombinations of fragments, the pore sizes of the resulting microclustes are ultimately polydisperse. The pore size distribution (PSD) measured for aggregates produced under shear RLCA (see FIG. 19b) is similarly narrow as that measured for monolith (see FIG. 21b, c). This gives us further possibility to tune PSD being broad for shear DLCA or narrow for shear RLCA.

Chromatographic columns packing: Macroporous microclusters were prepared using methods described above, i.e. DLCA as well as RLCA under shear. Obtained slurry with average diameter in the range from 50 to 80 microns was used in the further analysis. For both conditions formed slurry was pre-concentrated such that it contains 50% dry content using centrifugation. The stationary phases were packed in Tricorn 5/50 columns (GE Healthcare) using a HPLC pump PU 1580 (Jasco). In the packing procedure, depending on the available amount of media, the column length was varied between 4 and 5.5 cm. The experiments were performed on an Agilent 1100 HPLC system with multiple wave diode array UV and refractive index detectors.

Experimental procedures for stationary phase characterization: Inverse size exclusion chromatography (ISEC) was performed to determine the pore size distribution of the different stationary phases. Each dextran standard was injected by pulse at 0.5 mL/min in 30 mM phosphate buffer. The first moment of each chromatogram was used to determine the accessible volume as a function of the solute size. Injection of potassium chloride was used to measure the total porosity.

As can be seen the total porosity being around 80-85% is not changing with the increasing the dextran standard size confirming presence of very large pores. Similar results for the porosity around 90% were measured also for the aggregates produced through shear-induced RLCA procedure described above.

Surface Functionalization:

Due to large pore diameter results in a limited surface area available for separation two particular procedures were used to increase the capacity of the produced stationary phase. In particular, synthesis of charged brushes covalently bound to the surface of microclusters using ATRP, decoration of microcluster surface with oppositely charged nanoparticles having size much smaller than the inner diameter of the pores that are decorated (at least by a factor 10). In what follows both methods are described in details.

Surface Functionalization Through Synthesis of Charged Brushes Covalently Bound to the Surface of Microclusters:

A typical functionalization procedure using ATRP resulting in a formation of charged brushes on the surface of stationary phase is as follows. An unfunctionalized column (0.5×5.3 cm), packed with the macroporous microclusters (total porosity 85%) was mounted on a Metrohm offline HPLC pump and washed with pure water at 0.7 ml/min for at least 3 h prior to functionalization, of which 1.5 h was done with degassed water. Meanwhile the reaction mixture was prepared in a stoppered flask containing 103 mg of 2-Acrylamido-2-methylopropane sulphonic acid (AMPS) and 10 mg $NaNO_3$, dissolved in 20 ml $H_2O$. In the case of charged surface functionalization two other monomers were applied, i.e. N-isopropylacrylamide (NIPAM) and 2-(Acryloyloxy)ethyl trimethylammonium chloride (ATMA), with the amount of equal to 425 mg and 2,880 mg for NIPAM and ATMA, respectively. After bubbling $N_2$ while stirring for 40 min, 31 µl of the ligand 1,1,4,7,10,10-Hexamethyltriethylenetetramine (HMTETA) were injected, followed by 5.55 mg Cu(I)Cl. The $N_2$ bubbling was continued for another 40 min and subsequently 6.35 ml of this mixture was transferred to a degassed flask under $N_2$, which had been mounted on a closed loop with the washed column and the offline pump. The mixture was circulated through the column at ambient temperature for 18 h at 0.7 ml/min. After the reaction end, the column was washed with water, while samples from the reaction mixture before and after functionalization were diluted with pure water and filtered by flash chromatography through short silica gel columns to remove the reaction catalyst. Following filtration through 0.45 µm PTFE syringe filters, the two samples were analyzed by HPLC through a YMC ODS-AM-303 S-5 µm C8 column flown with 50 mM Phosphate buffer pH6.0, containing 1% v/v acetonitrile (ACN) at 1 ml/min. The monomer conversion was calculated by comparing the monomeric AMPS peak areas at 230 nm before and after functionalization, using the $NO_3^-$ peaks as internal standards. Moreover, these samples were analyzed by Gel Permeation Chromatography (GPC) at 25° C., through a Waters Ultrahydrogel Linear column (7.8 mm×30 cm), flown with 0.1M $NaNO_3$ at 0.5 ml/min. Monitoring the RI signal confirmed the absence of any polymer in the bulk solution, i.e. grown in solution following chain transfer or detached from the column, therefore the complete amount of converted monomer determined by HPLC should correspond to PAMPS grafted on the column. The grafting amount for different columns was controlled by varying the amount of monomer loaded initially. To show performance of the presented material two commercial stationary phases were chosen for comparison with the novel materials, Fractogel EMD SO3 (M) (Merck KGaA) as a preparative chromatography adsorbent with high binding capacity and Poros 50HS (Applied Biosystem) as a perfusive material produced by suspension polymerization. The characteristics of the five considered stationary phases are summarized in Table 6.

TABLE 6

Functionalization characteristics of the various considered particles:

| Stationary phase name | Average particle size (µm) | $\sigma_p$ (# of brushes/ $nm^2$) | Degree of polymerization for single brush (—) | Surface charge density (mmol $SO_3^-$/mL col) |
|---|---|---|---|---|
| Fractogel EMD $SO_3$ (M) | 65 | not available | not available | 0.138 |
| Poros 50HS | 50 | no brush | no brush | 0.117 |
| Perf0 | 70 | no brush | no brush | 0 |
| Perf1 | 65 | 0.187 | 244 | 0.039 |
| Perf2 | 64 | 0.187 | 335 | 0.112 |
| Perf3 | 56 | 0.374 | 220 | 0.235 |

Perf0 was not functionalized, whereas on the other three, brushes bearing multiple sulfonate groups were grafted. The difference between Perf1, Perf2, and Perf3 is the brush density on the intra and extra particle surface, which can be controlled by the number of initiator positions on the particle surface and the length of a single brush, defined by the degree of polymerization. In particular, Perf2 is considered as the reference, having comparable surface charge density with both commercial materials, while Perf1 has lower surface charge density, owing to reduced brush length, and Perf3 has a brush density twice as high as Perf1, exhibiting thus the highest surface charge density.

Particle morphology: As shown in Table 6, all the stationary phases used have a comparable average particle size in the range of 50 to 70 microns and their surface is covered by SO; groups except Perf0 which is non-functionalized. On the other hand, the two commercial materials (Fractogel EMD SO3 (M) and Poros 50HS), as well as the novel brush macro-porous adsorbent Perf2 have similar surface charge densities, while Perf1 and Perf3 exhibit lower and higher surface charge density, respectively. In FIG. 22, the measured column porosity for all the investigated stationary phases is shown as a function of the dextran probe radii. It can be seen that the total porosities of the five tested stationary phases measured for the smallest dextran are similar and lie between 0.75 and 0.83 (see first column in Table 7), which are typical values for ion-exchange chromatography materials.

TABLE 7

Porosity values for the various considered particles. $\varepsilon_{total}$ is the total column porosity, is the column porosity measured for the largest dextran (37 nm radius)

| Stationary phase name | $\varepsilon_{total}$ (—) | $\varepsilon_{macro}$ (—) |
|---|---|---|
| Fractogel EMD SO$_3$ (M) | 0.78 | 0.40 |
| Poros 50HS | 0.75 | 0.40 |
| Perf0 | 0.83 | 0.83 |
| Perf1 | 0.80 | 0.68 |
| Perf2 | 0.80 | 0.58 |
| Perf3 | 0.78 | 0.50 |

Moreover, with the only exception of Perf0, the measured porosity for all stationary phases decreases with increasing size of the dextran standards, clearly indicating reduced pore accessibility for larger probes. In the case of Fractogel EMD SO3 (M) and Poros 50HS the measured decrease is more pronounced compared to Perf1, Perf2, Perf3. Moreover, for the largest dextran standard with radius of 37 nm the accessible porosity reaches values around 0.4, which is a typical value for bed porosity. This corresponds therefore to zero intra-particle porosity.

The constant column porosity equal to about 0.83 measured for Perf0 for all considered dextran sizes indicates the presence of very large pores. This is in agreement with mercury intrusion porosimetry values, where an average pore radius around 500 nm was measured. However, such large pores become smaller after functionalization, as indicated by the decrease of porosity measured for all functionalized stationary phases (Perf1, Perf2, Perf3) with larger dextran standards (see FIG. 22). For any given dextran size, the accessible porosity for Perf2 is smaller than the corresponding one for Perf1, owing to the longer grafted brushes on Perf2. Perf3 exhibits even lower porosity values, presumably due to the larger grafting density of brushes on Perf3, which results in larger chain stretching and hence thicker grafted layer. Actually, the smallest column porosity value determined for Perf1 with the largest dextran (radius of 37 nm) is 0.68, while for Perf3 is 0.5. When considering a packed bed porosity of 0.4, these values indicate that about 70 to 25% of the pores are accessible by the 37 nm dextran.

It is worth noting that the column pressure drop is not affected by the perfusion because the reduction of the extra-particle flow due to perfusion is negligible. In this report, all the stationary phases have similar particle size, and therefore the column pressure drops are expected to be similar as it is confirmed by the column pressure drop data in FIG. 23.

Intraparticle mass transfer resistances: The HETPs were measured for pulse injections of HSA and saccharose at various velocities between 0.1 and 2 mL/min. The first and second moments of the chromatograms were extracted to compute the HETPs. The performance of the column was investigated under non-adsorbing conditions with 30 mM phosphate buffer containing 1 M sodium chloride. The dextrans were detected with a refractive index detector. Comparison of the measured values for the non-functionalized columns obtained by DLCA under shear is presented in FIG. 24. The presence of large pores in the new stationary phases is expected to increase the mass transfer inside the particles. This is because the pore diffusion depends on the ratio between molecule and pore size, meaning that the mass transfer in larger pores is enhanced. Even more important, in sufficiently large pores a part of the flow can perfuse through the particle, and therefore significantly decrease the mass transfer resistance in the particles. In the sequel, the HETP values of each column measured as a function of the interstitial velocity was studied using a small molecule, saccharose, and a protein, HSA, both under non-adsorbing conditions. The obtained results of HETP versus interstitial velocity are shown in FIG. 24 in reduced form using the following quantities:

$$h = \frac{H}{2R_p} \text{ and } v' = \frac{2R_p}{D_m} v \qquad (8)$$

with h being the reduced HETP and v' the reduced interstitial velocity. It is worth noting that such reduced form allows direct comparison among different columns, independently of the particle size and the solute diffusion coefficient. As can be seen in FIG. 24a, for all columns the reduced HETP for saccharose increases monotonically with increasing reduced velocity. In particular, the increase of HETP as a function of interstitial velocity is linear for Fractogel EMD SO3, in agreement with models as confirmed by the dotted line in FIG. 24a. The HETP increase with velocity is less pronounced for Poros 50HS as well as for the novel macroporous materials. In particular, these exhibit a bending for larger velocity values which can be attributed to some perfusion contribution, although a clear constant plateau with constant HETP for increasing velocity is only achieved by one of them, i.e. Perf3.

The HETP values for the much larger protein HSA are shown in FIG. 24b. Due to its lower diffusion coefficient compared to saccharose, not only the corresponding measured HETP values are larger but also the perfusion effect is now more evident. In particular, the reduced HETP values for Fractogel EMD SO3 (M) still exhibit a strong linear increase with velocity, again well fitted by models as shown by the dotted straight line in FIG. 24b, which confirms that pore diffusion is the limiting mass transfer rate and that no perfusion is present. On the other hand, for all four new materials the HETP values are only slightly affected by the flow rate increase, with an almost flat HETP curve typical of perfusive materials. It is worth mentioning that since Perf0 is not functionalized, there are strong hydrophobic interactions between HSA and the particle surface, resulting in irreversible adsorption. Therefore, in order to compare the performance of this stationary phase to that of the functionalized ones, a dextran standard with molecular weight of 50 kDa with a similar radius equal to 5.1 nm was used instead of HSA. Finally, the HETP values for Poros 50HS exhibit a behavior somehow in between the new materials and Fractogel EMD SO3 (M), indicating a partial perfusing behavior which can nevertheless lead to significantly reduced HETP values particularly at the highest velocities. Also in this case of perfuse materials, the experimental data have been compared with models for the evaluation of the $C_{perf}$ coefficient. In FIGS. 24c and d such a comparison is shown with illustrative purposes for Poros 50HS and Perf2.

As mentioned above, in order to quantitatively investigate the role of perfusion evidenced by the above experimental results, the Van Deemter data shown in FIG. 24 for the six different stationary phases and the two molecules, saccharose and HSA, have been compared with model simulations for diffusive or perfusive particles, respectively. The fitted values have been determined for both solutes, to find that the model describes well the experimental data with an error being below 10% for all experimental conditions.

TABLE 8

Fitted parameters for the perfusive HETP profile

| Stationary phase name | Solute | A (cm) | F (—) | $D_{eff}$ (cm²/min) | error % | τ (—) | Pe*$_{perf}$ (—) | $r_{pore}$ (nm) |
|---|---|---|---|---|---|---|---|---|
| Fractogel EMD SO₃ (M) | Saccharose | 0.03 | 0 | $8.9 \times 10^{-5}$ | 3.2 | 2.7 | 0 | — |
|  | HSA | 0.01 |  | $2.5 \times 10^{-6}$ | 8.3 | 16.4 | 0 |  |
| Poros 50HS | Saccharose | 0.022 | $7.4 \times 10^{-4}$ | $6.9 \times 10^{-5}$ | 5.3 | 3.5 | 0.1 | 89 |
|  | HSA | 0.027 |  | $4.9 \times 10^{-6}$ | 1.3 | 8.4 | 1.0 |  |
| Perf0 | Saccharose | 0.025 | $2.0 \times 10^{-2}$ | $1.3 \times 10^{-4}$ | 4.4 | 1.9 | 1.4 | 360 |
|  | Dextran 50 kDa | 0.034 |  | $2.2 \times 10^{-5}$ | 3.3 | 1.0 | 8.5 |  |
| Perf1 | Saccharose | 0.031 | $1.1 \times 10^{-2}$ | $1.6 \times 10^{-4}$ | 4.0 | 1.5 | 0.6 | 292 |
|  | HSA | 0.038 |  | $2.5 \times 10^{-5}$ | 3.0 | 1.6 | 3.5 |  |
| Perf2 | Saccharose | 0.021 | $1.4 \times 10^{-2}$ | $1.4 \times 10^{-4}$ | 4.3 | 1.6 | 0.8 | 330 |
|  | HSA | 0.027 |  | $2.0 \times 10^{-5}$ | 3.5 | 2.1 | 6.0 |  |
| Perf3 | Saccharose | 0.017 | $1.5 \times 10^{-2}$ | $2.2 \times 10^{-4}$ | 9.1 | 1.1 | 0.5 | 325 |
|  | HSA | 0.015 |  | $1.3 \times 10^{-5}$ | 2.5 | 3.2 | 8.4 |  |

In Table 8 A is the eddy diffusion term coefficient, F the perfusive flow fraction (–), $D_{eff}$ is the pore effective diffusion coefficient (cm²/min), τ is the tortuosity coefficient (–) Pe*$_{perf}$ the perfusive peclet number (–), $r_{pore}$ the pore radius (cm).

The first fitted parameter on the HETP curve is the eddy diffusion term A that is independent of the perfusive character of the stationary phase. The coefficient values for A summarized in Table 8 are similar for the six considered columns. It is worth noting that these values are relatively high and could be explained by the rather short length of the columns that makes significant the column wall effect on the flow dispersion.

The second fitted value reported in Table 8, is the perfusive flow fraction F. As can be seen, larger values of F correspond to smaller values of the HETP plateau in FIG. 24. Indeed, the higher the perfusion, the better the mass transfer, i.e. the lower the HETP. With F equal zero, the material Fractogel EMD SO3 has no perfusion effect present in the particle. With perfusive flow fractions F between 0.01 and 0.02, the novel stationary phases Perf0, Perf1, Perf2 and Perf3 exhibit typical HETP values for perfusive particles with a plateau for HSA at high velocities. In the case of Poros 50HS rather low perfusive flow fraction compared to the four considered novel materials was found, explaining the slight bended shape of its HETP values shown in FIG. 24d. The perfusion level in this particle is high enough to exhibit higher mass transport compared to non perfusive particles but it is still too low to reach a HETP value independent of the flow rate in the range of the considered velocity values.

The third parameter obtained from fitting the HETP data is the effective diffusion coefficient. As can be seen in Table 8, in all cases the values of $D_{eff}$ are smaller than the bulk molecular diffusivity for saccharose and HSA, $D_m$, equal to 2.4×10-4 cm2/min and 4.1×10-5 cm2/min, respectively. The differences of $D_{eff}$ for the different stationary phases, as well as from $D_m$ can be related to the effect of the pore structure and of the ratio of the pore and solute radii on mass transfer. To characterize this effect, the tortuosity factor is defined as the ratio between the bulk diffusion coefficient and the corresponding effective diffusion coefficient:

$$\tau = \frac{D_m}{D_{eff}} \quad (9)$$

As seen from Table 8, the tortuosity coefficient for saccharose is in all cases low, between 1.1 and 3.2, which are common tortuosity values for small molecules. It shows that for saccharose the ratio between the pore and solute radii does not influence the mass transfer because saccharose is much smaller than the pores of all the considered stationary phases. On the other hand, for HSA this coefficient is strongly affected by the type of stationary phase. In particular, for Fractogel EMD SO3 this value is equal to 17.1, which is consistent with those found in the literature for this specific packing material, while in the case of Poros 50HS it reduces to 8.4. For the novel materials the tortuosity value is significantly smaller, between 3.2 and 1.6. The difference in the pore structure has therefore a high impact on the mass transfer properties and consequently also on the column performance. This behavior may also be explained by considering that the pore tortuosity τ is affected by the ratio of the pore and solute radii. When this is large enough, like in the new particles, it has no effect, while when it gets smaller as for Poros 50HS and even more for Fractogel EMD SO3 then it plays an important role leading to much larger values of tortuosity as the ones reported above.

For completeness in Table 8, are also reported the values of the perfusive Peclet number computed at 1 mL/min with Eq.(4) using the fitted model parameters, F and $D_{eff}$, so as to have a quantitative measure of the importance of the perfusive flow on the rate of intra-particle mass transfer. As expected from the shape of the HETP curves in FIG. 24a, the perfusive Peclet number at 1 mL/min for saccharose obtained for Poros 50HS is substantially below 1.0, indicating that convection has a negligible effect on mass transfer. On the other hand, values around 1.0, covering a range from 0.5 to 1.4 were obtained for the novel macro-porous materials Perf0, Perf1, Perf2 and Perf3, indicating that under the investigated conditions the effect of convection through the pores is of the same order as that of diffusion. In contrast, for HSA the perfusive Peclet number is larger than 1.0 for all perfusive materials including Poros 50HS. However, the values of the perfusive Peclet number indicate that the new stationary phases Perf1, Perf2 and Perf3 exhibit a much stronger effect due to perfusion than Poros 50HS in agreement with all above results.

It is worth noting that the fraction of perfusive flow F, as a function of the bed and particle porosities and of the ratio between particle and pore radii, can give qualitative information about the effective average pore size in the particle, rpore. As can be seen from Table 8 in the case of Poros 50HS, the obtained pore radius was found to be equal to 89 nm, while in the case of all the three novel functionalized stationary phases Perf1, Perf2 and Perf3 an average pore radius of around 315 nm was obtained (Table 8). This value is smaller than that obtained for the non-functionalized material Perf0, equal to 360 nm, which is in agreement with the reduction of the experimental porosity values, shown in FIG. 22 for larger dextran standards. Both trends indicate that the presence of brushes has a steric impact on the pore accessibility, while it does not reduce the perfusive flow fraction substantially. Furthermore, it is worth noting that, since in the theory of perfusion through large pores, it was assumed that all pores have the same size, the obtained results should be considered as an indicative of the perfusive transport in the particles. In light of this assumption, the obtained values for the effective pore radius agree reasonably well with the average pore radius of the non-functionalized adsorbent measured by mercury intrusion porosimetry, where a broad distribution with an average pore radius around 500 nm was obtained.

Based on the above results it can be concluded that for large molecules, i,e. HSA, the newly synthesized stationary phases exhibit a superior performance (i.e. smaller HETP values) compared to the other two considered commercial stationary phases. This is due to their lower ratio $D_m/D_{eff}$ and to flow perfusion inside the particles which result in a strong reduction of the mass transfer resistance.

Surface Decoration Using Oppositely Charge Small Nano-particles

Sulphonation of polystyrene aggregates is achieved by slowly adding 200 mL of preformed micro-particles suspension to 250 mL of gently stirred 97% sulphuric acid. This process is very exothermal and should be done carefully; the usually preferred way of adding the acid to the aqueous solution produces large amounts of aggregates. The system is kept stirring for 24 hours at 80° C. The particles are then thoroughly washed with water. This concludes the preparation of the support material.

Anion exchange capacity is introduced to the resin by electrostatically fixating positively charged latex particles. These particles are produced via emulsion polymerisation and subsequently aminated. The emulsion polymerisation is carried out in a 250 mL 3-neck round-bottom flask equipped with magnetic stirrer and reflux condenser. It is charged with a solution of 0.3 g SDS in 90 mL of water that has been stripped with nitrogen for 20 minutes. Then, glycidyl methracrylate (5 g) and ethylene glycol dimethracylate (1 g) are added. The system is heated to 70° C. and purged with nitrogen for 10 minutes. Then, 0.2 g KPS in 10 mL water are added to start the reaction. After 4 hours the reaction is stopped by cooling down the flask in an ice bath. After filtering the latex through a cellulose filter, it is mixed with 100 mL of dimethylethylamine and stirred for 18 hours at 50° C. This reaction can produce some latex particle aggregates that can be broken and the primary particles re-dispersed using ultrasonication (30 min, 0.5 s on/0.5 s off cycle, 50% strength), yielding a z-average particle diameter of 74 nm and PDI of 0.036 as determined by dynamic light scattering.

Combination of the anion exchange latex and the sulphonated support is achieved by diluting the slurry such that the support is present at 5 weight-percent. 50 mL of this suspension are then gently stirred in a beaker. 14 mL amine latex with particle size of 74 nm are now added dropwise (1 drop/per second); after addition is complete, the system is kept stirring for another 30 min. The resulting slurry is then washed 5 times with 90 mL of water or longer until the wash is clear of latex.

Figure 25:
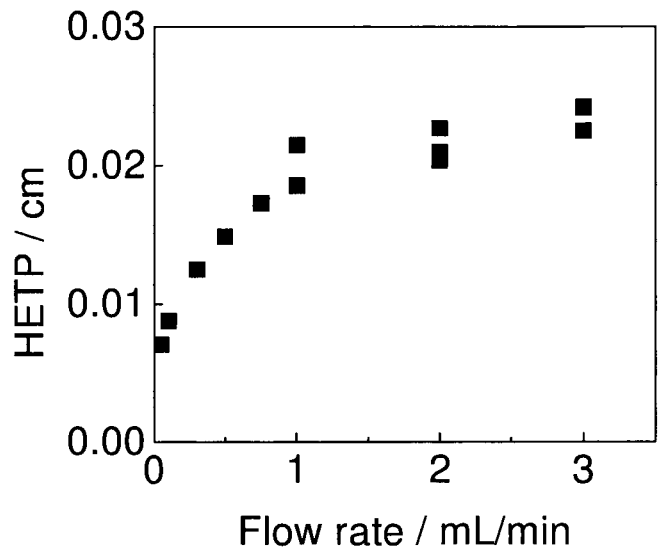
FIG. 25 shows the van Deemter plot for potassium chloride on perfusive material

The van Deemter plot (FIG. 25), showing the dependency of the height equivalent of a theoretical plate (HETP) on the flow rate was measured by injecting pulses of potassium chloride on a non-functionalized column (4 mm i.d.×100 mm). HETP were calculated from the conductivity peak first and second moments, subtracting equipment-induced peak broadening. Pressure drop over the column was below the sensor detection limit of 1 bar for all experiments.

The functional density of sulphonic acid groups is determined by chromatographic breakthrough experiments carried out at 1 mL/min. The column is acidified with 10 mmol/L $HNO_3$ for 25 minutes, then flushed with milli-Q water for 25 minutes. Having replaced adsorbed cations by $H^+$ and flushed out non-adsorbed $H^+$, the capacity is determined by desorbing the $H^+$ with $K^+$ in the form of 1 mmol/L $KNO_3$ and integrating from the chromatogram to obtain a column capacity of 3.4 μeq/mL.

After having decorated the support with anion exchange latex, the anion exchange capacity was determined in similar experiments, again at 1 mL/min. First, all quaternary ammonium groups are associated with a chloride ion by flushing 50 mmol/L NaCl for 30 minutes, then the pore void space is flushed with milli-Q water to remove all non-adsorbed anions. The chloride ions are then replaced by $OH^-$ using 1 mmol/L NaOH and the breakthrough is integrated to obtain a column capacity 38.5 μeq/mL. To show that this capacity is indeed inside the pores and not only on the surface of the particles, it can be normalized with the particle geometric surface area assuming spheres and compared to a non-porous material that was sulphonated and decorated in the same manner. The non-porous material yields 22 μeq/m² geometric surface area, whereas the macro-porous material gives 353 μeq/m² geometric surface area. This clearly indicates substantial additional intra-particle surface area compared to non-porous particles.

Chromatographic Applications—Peptide/Protein Separation

In this part, the use of the macro porous micro-clusters as macro-porous chromatographic stationary phases shall be illustrated, combining low mass transfer resistance and high binding capacity. The new stationary phases exhibit better performance compared to commercially available materials, i.e. Poros 50HS and Fractogel EMD SO3 (M). With the new technique of reactive gelation under shear, it is possible to produce particles with pores from 100 nm to several microns, in which part of the flow can go through. This way, the mass transport inside the particles is significantly increased. Despite the low pore surface area resulting from the large pore size, high binding capacity is obtained by functionalizing the pore surface with charged polymeric brushes. This, together with the high mass transfer, gives excellent resolution performance and dynamic binding capacity compared to other commercial materials. Polyelectrolyte brushes are grafted onto the surface of the particles generated using a method according to the invention via flow-through Atom-Transfer Radical Polymerization (ATRP), so that electrostatic interactions become effective. An advantage of this technique with respect to the commonly used functionalization methods, with which a single charged group is located directly on the pore surface, is that the pores are covered with brushes containing several charged groups, offering a higher binding capacity. A comparison is shown with classical commercial materials: Poros 50HS, which are perfusive particles with no brushes and Fractogel EMD SO3 (M) which are non perfusive particles containing brushes, showing the synergisms between brushes, the improvement in capacity, and perfusive characteristics, and the improved transport characteristics.

Experimental:

Chemicals: All experiments have been performed with a 30 mM phosphate buffer at pH 7. The buffers were prepared by mixing sodium phosphate dibasic (Sigma-Aldrich) and sodium phosphate monobasic (Fluka) in the required proportion to get the desired pH. Sodium Chloride (Prolabo) was used to modify the ionic strength of the buffers. The chemicals were mixed in deionized water from a Millipore Mill-Q system and filtered with 0.45 μm durapore membrane filter (Millipore). For the protein separation experiments an artificial mixture of lysozyme (Fluka), cytochrome c (Acros) and chymotrypsinogen alpha (Applichem) was prepared at a concentration of 1 mg/ml for each protein in 30 mM phosphate buffer at pH 7. For the breakthrough experiments, a lysozyme solution was prepared at 5 mg/ml. All protein solutions were filtered with 0.45 μm durapore membrane filters. Human Serum Albumin—HSA (Sigma) and saccharose (Chemie Brunschwig) were used for the HETP measurements and a set of nine dextran standards for the Inverse Size Exclusion Chromatography (ISEC) experiments.

Chromatographic resolution: For the resolution measurements, the columns were operated under a linear salt gradient. In order to compare directly the chromatograms of columns with different length, it is necessary to apply the same normalized salt gradient γ defined as:

$$\gamma = \frac{\Delta C_M L}{t_G v}$$

where $\Delta C_M$ is the difference of salt concentration between the beginning and the end of the gradient and $t_G$ is the duration of the gradient. Pulse injections of the model protein mixture containing lysozyme, chymotrypsinogen alpha and cytochrome c were carried out at 1 and 2 mL/min under linear salt gradient conditions (from 0 to 1 M NaCl in 30 mM phosphate buffer). The normalized gradient slope γ=43.2 was chosen, which corresponds to a gradient duration of nine minutes at 1 mL/min in a column length of 5 cm. UV signals at 280 nm and 400 nm were recorded at the column outlet. Since the cytochrome c is the only protein of the mixture that can also absorb at a wavelength equal to 400 nm this was used when the three proteins were not baseline separated and a decorrelation of the UV signal at 280 nm was done by using the concentration profile of cytochrome c measured at 400 nm. This decorrelation was possible because lysozyme and chymotrypsinogen alpha do not overlap in all the experiments in this work.

The breakthrough experiments were carried out at 0.5 and 2 mL/min with a solution of lysozyme at 5 mg/mL in 30 mM phosphate buffer at pH 7. The equilibrium binding capacity was estimated from the breakthrough curves after reaching equilibrium conditions. On the other hand, the 10% dynamic binding capacity was measured for both flow rates. The profile of the experiment was recorded at two wave lengths: 300 and 310 nm to exclude saturation conditions.

Figure 26:
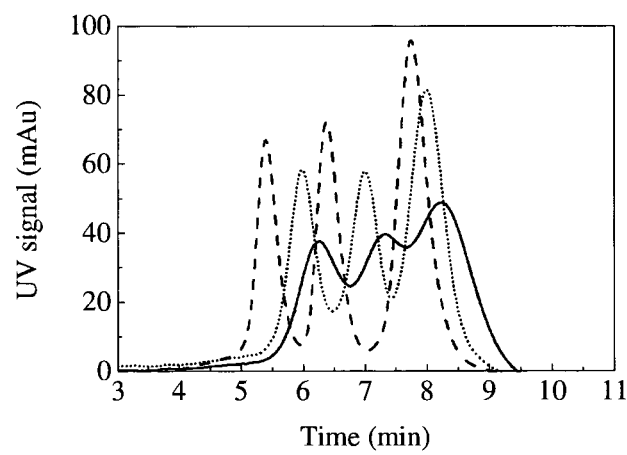
FIG. 26 shows the chromatograms of model protein mixture separation under the same normalized salt gradient elution using Fractogel EMD SO3 (M) (continuous line), Poros 50HS (dot line) and Perf2 (dashed line)
Figure 27:
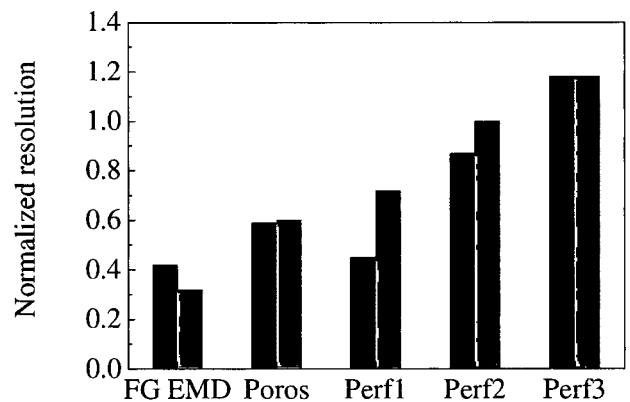
FIG. 27 shows the normalized resolution, $r_s$ given by Eq.(10) with the same normalized salt gradient elution, measured for a flow rate of 1 mL/min, between chymotrypsinogen alpha and cytochrome c (black columns) and between cytochrome c and lysozyme (grey columns)

As a further comparison of the performance capabilities of the various stationary phases considered in this section, the different columns were compared with respect to the separation of a model mixture of three proteins (lysozyme, chymotrypsinogen alpha and cytochrome c), performed with a salt gradient elution at a flow rate of 1 mL/min. For comparison purposes, the separations were carried out keeping the same normalized gradient, such as to account for the different column lengths (ranging between 4 and 5.5 cm). Illustrative chromatograms corresponding to Fractogel EMD SO3, Poros 50HS, and Perf2 are shown in FIG. 26. The first eluting protein is chymotrypsinogen alpha, followed by cytochrome c and lysozyme. There is a clear difference in the resolution capabilities of the three stationary phases. In particular, Fractogel EMD SO3 (M) exhibits the lowest resolution, as the three peaks do not reach baseline separation under the applied conditions, followed by Poros 50HS and Perf2, which are capable to separate the protein mixture more efficiently, especially Perf2 which exhibits baseline separation. To properly compare the separation efficiency of columns with different lengths, a normalized resolution coefficient, independent of the column length was considered as follows:

$$r_s = \frac{R_s}{\sqrt{L}} \tag{10}$$

where Rs represents the resolution coefficient, computed through models, which is known to increase with the square root of the column length. FIG. 27 shows a comparison of the obtained values for the normalized resolutions between chymotrypsinogen alpha and cytochrome c, as well as between cytochrome c and lysozyme, for all considered materials measured at a flow rate of 1 mL/min. It is worth noting that the normalized column resolution increases with decreasing values of HETP measured for each materials as shown in FIG. 24. This confirms the expected strong impact of mass transfer on resolution. The normalized resolutions of the novel macro-porous stationary phases range from 0.5 to 1.2, whereas for Poros 50HS and Fractogel EMD SO3 (M) are equal to 0.55 and 0.35, respectively. It can also be seen that the normalized resolution of the novel macro-porous stationary phases increases with increasing surface charge density (see FIG. 27 and Table 9).

In order to better quantify the effect of column efficiency on resolution, further experiments were performed at 2 mL/min, using the same normalized salt gradient as in the previous runs at 1 mL/min. Since column Perf3 could not withstand this flow rate, it was excluded from the following analysis. In Table 9 the percentage decrease between the normalized resolutions going from 1 to 2 mL/min for four of the considered materials is reported.

TABLE 9

Normalized resolution decrease percentage upon increasing the flow rate from 1 to 2 mL/min

| Separated Solutes | Perf1 | Perf2 | Poros 50HS | Fractogel EMD SO₃ (M) |
|---|---|---|---|---|
| Chymotrypsinogen alpha/Cytochrome c | 16% | 14% | 25% | 31% |
| Cytochrome c/Lysozyme | 14% | 14% | 28% | 28% |

As the normalized gradient is the same at both velocities, the retention volume for each molecule is conserved. Accordingly, the decrease in resolution is therefore due to the performance reduction at larger velocities. This is confirmed by the fact that for both solutes combinations, the decrease is similar for each given column. It appears that Perf1 and Perf2, having the lowest HETPs, exhibit the smallest resolution decrease, whereas Fractogel EMD SO3 (M) exhibits the largest one. The percentage decrease is consistent with the HETP values for each stationary phase.

Dynamic binding capacity: The perfusive effect can help also in improving the Dynamic Binding Capacity (DBC) of the columns. For proteins, this quantity is a delicate compromise between equilibrium binding capacity (EBC) proportional to the pore surface, i.e. inverse proportional to the pore size $r_{pore}$, and mass transfer proportional to the pore size $r_{pore}$. As we have seen above, in large pores perfusion provides more effective mass transport for proteins, and the use of polymeric brushes is a good alternative to enable high EBC despite having a low pore surface.

Figure 28:
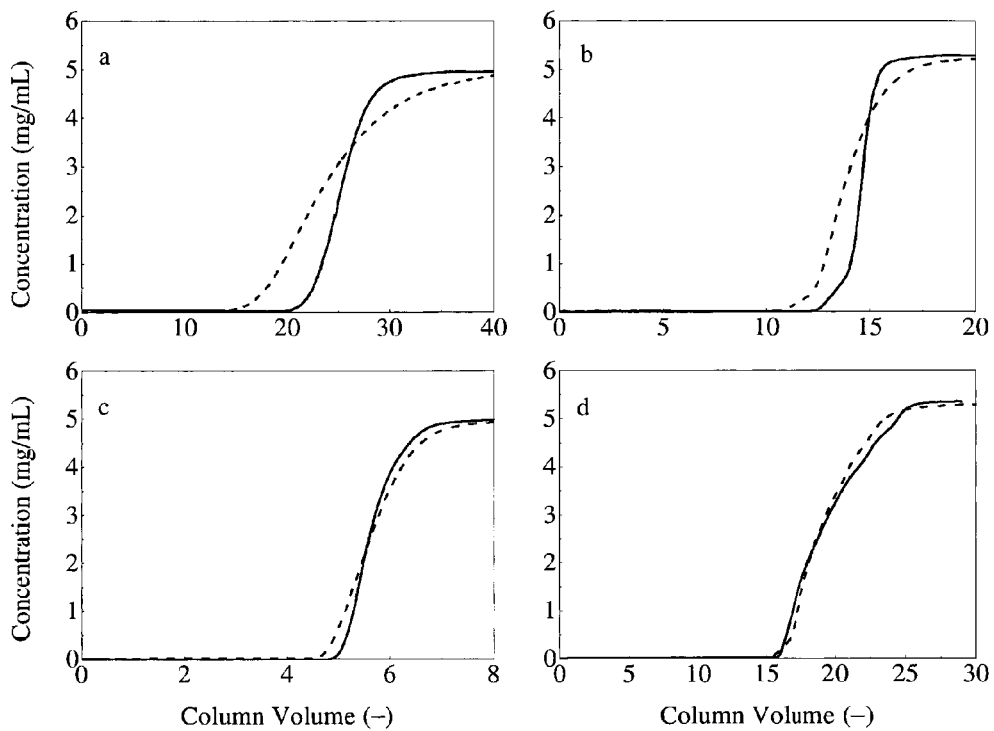
FIG. 28 shows the breakthrough curves of lysozyme at 0.5 mL/min (solid lines) and 2 mL/min (dotted lines) for four of the considered columns: a) Fractogel same normalized salt gradient elution using Fractogel EMD SO3 (M) (continuous line), Poros 50HS (dot line) and Perf2 (dashed line) EMD SO3 (M), b) Poros 50HS, c) Perf1 and d) Perf2

The dynamic binding capacity was measured for all columns at 0.5 and 2 mL/min, except Perf3 that was not mechanically stable at 2 mL/min. As can be seen from FIG. 28, the breakthrough curves of Fractogel EMD SO3 (M) are strongly affected by the flow rate, owing to the pore diffusion resistance. Poros 50HS exhibits an intermediate dependency, while the shapes of the breakthrough curves measured for Perf1 and Perf2 are scarcely affected by the flow rate. These results are in agreement with the flat HETP profiles shown in FIG. 24.

Figure 29:
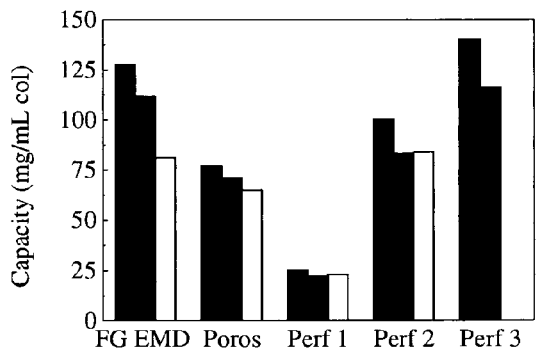
FIG. 29 shows the binding capacities of lysozyme for the various considered stationary phases. Black: equilibrium binding capacity. Grey: 10% dynamic binding capacity at 0.5 mL/min. white: 10% dynamic binding capacity at 2.0 mL/min
Figure 30:
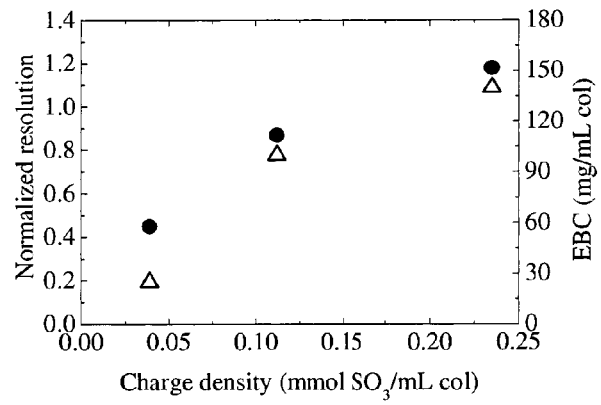
FIG. 30 shows the normalised resolution $r_s$ (●) and equilibrium binding capacity EBC (Δ) as a function of the charge density of each of the novel considered stationary phases

When comparing the equilibrium binding capacity, it can be seen in FIG. 29 that Fractogel EMD SO3 (M) and Perf3, with their high charge density exhibit the highest binding capacity followed by Perf2, Poros 50HS and Perf1. Moreover, for Fractogel EMD SO3 (M), the effect of mass transfer on the DBC is strongly pronounced. Its 10% DBC decreases by 27% going from 0.5 to 2 mL/min, whereas this decrease is only about 8% for Poros 50HS and no decrease was observed for Perf1 and Perf2. This is again consistent with the HETP profiles described previously in FIG. 24. However, it has to be noted that for Perf2 and Perf3, the 10% DBC at 0.5 mL/min is approximately 20% smaller than its EBC, which is a decrease similar to that observed for Fractogel EMD SO3. This is somehow unexpected since the mass transfer resistance in the Perf2 and Perf3 particles is low, as indicated by the low HETP. Since such a decrease is not observed for Perf1 particles, it could be related to the presence of longer brushes, which could slow down the adsorption and mass transfer kinetics close to saturation conditions due to steric crowding. It is worth noting that in the material Perf2, the charge density is similar to Fractogel EMD SO3 (M) providing similar high equilibrium binding capacity. Let us now analyze qualitatively the impact of surface charge density of each considered novel material on the equilibrium binding capacity and on the normalized resolution $R_s$. As can be seen from FIG. 30 the EBC and the resolution clearly increase with the density of charges. From these data, no specific effect can be observed from the brush length (Perf2 has longer brushes) or from the brush density (Perf3 has denser brushes on the pore surface). The obtained data also indicate that there is still a potential to further increase the resolution and the equilibrium capacity by increasing the charge density of the particle as no clear plateau has been reached in the considered range of charge density.

Thus summarizing, the obtained results show that the novel macro-porous particles combine the perfusive effect with a charge density similar to Fractogel EMD SO3 (M), which makes them ideal candidates for bind-elute process of proteins, as they combine high binding capacity and negligible mass transfer resistance so as to lead to optimum dynamic capacities.

Conclusion: The stationary phase Poros 50HS is a stationary phase of choice in protein purification because it has good mass transfer properties due to perfusion through large pores. On the other hand, the stationary phase Fractogel EMD SO3 (M) is also of interest in protein purification because it has a high binding capacity due to the polymeric brushes grafted on the pore surface. The new technique of reactive gelation has been utilized in this work to produce a novel stationary phase that combines both these advantages. The properties and possible chromatographic applications of this novel macro-porous material have been investigated and compared to the two commercial materials Poros 50HS and Fractogel EMD SO3 (M). The chromatographic separation capabilities of the new particles are superior to the commercial stationary phases due to reduced mass transfer resistance inside the particles promoting perfusion through the macro-pores, while the use of brushes provides high equilibrium capacity in spite of the large pore sizes. Consequently, these media possess a high resolution power and can have optimal performances in protein chromatographic purification processes. Moreover, high equilibrium binding capacities comparable to Fractogel EMD SO3 (M) together with the perfusive properties lead to high dynamic binding capacities for the novel materials also at high flow rates, making them ideal also for capture step applications.

Application of Anion Exchange Gel Impregnated Particles for Small Ion Separation:

The macro porous micro-clusters were prepared by the seeded emulsion polymerization as described above. After surface decoration with amine groups formed micro-clusters were packed into a PEEK column of size 4 mm i.d.×250 mm using the following method. A slurry of 50% vol. particles is well dispersed and then placed in the PEEK column and an attached reservoir on top. The column is closed on the bottom with a cellulose frit. Then, 30 bar air pressure are applied on top until all liquid has left the column through the frit. The pressure is closed and the system left to expand for 5 minutes. The column is then closed on top with another fit and washed with 1.2 mM $Na_2CO_3$, 3.8 mM $NaHCO_3$ eluent over night. This column can then be applied in the separation of anions in aqueous solution. For this purpose, the column is installed in an ion chromatography unit, ideally with cation suppression (such as the Metrohm Professional 850, Herisau, Switzerland) and the system equilibrated to the above mentioned carbonate buffer. A 20 µL injection of 7 standard anions could be baseline separated with pressure drop of 5 bar at 1 mL/min over a 4×250 mm column. For comparison, a standard anion exchange resin, e.g. a Metrohm Metrosep A Supp 5, would have a pressure drop of 165 bar at comparable conditions, although providing better separation performance in terms of column efficiency. However, due to the flow-rate independent HETP (see FIG. 25) and low pressure drop at elevated flow rates, this column can be used with high eluent through-put and still low pressures for uncomplicated, quick separations with relatively cheap, low-pressure equipment.

Figure 31:
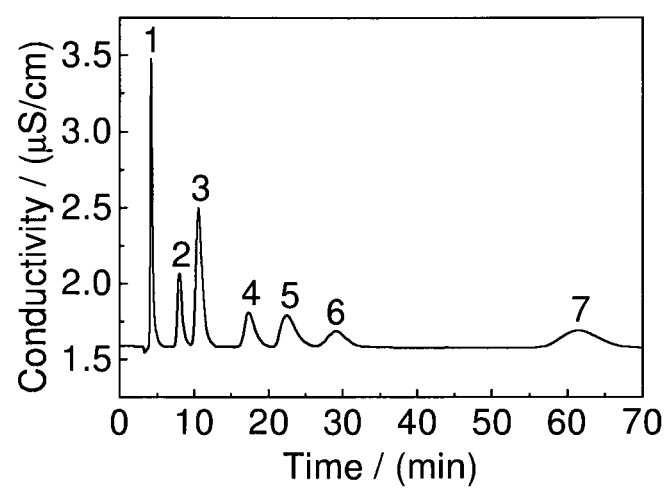
FIG. 31 shows a separation of 20 μL aqueous solution of 7 standard anions (1: 2 ppm fluoride, 2: 5 ppm chloride, 3: 5 ppm nitrite, 4: 10 ppm phosphate, 5: 10 ppm bromide, 6: 10 ppm nitrate, 7: 10 ppm sulphate) at 1 mL/min.

As it can be seen from FIG. 31 a baseline separation of a mixture of 7 standard anions in water, using a sodium carbonate eluent (1.2 mM $Na_2CO_3$, 3.8 mM $NaHCO_3$) at 1 mL/min using a Metrohm Professional 850 ion chromatography unit was achieved. It is worth noting that when comparing specific pressure drop of used column for a given superficial velocity measured values are at least 2 orders of magnitude lower compared to those obtained in commercial materials using very small particles with very small pores. This is significant advantage since hardware operating at much lower pressures can be used resulting in substantial reduction of investment and operation cost.

The invention claimed is:

1. A method for producing macro porous micro-clusters comprising at least the following individual steps in given order:
   a) synthesis of dispersed cross-linked polymeric latex primary particles starting from at least one monomer or oligomer;
   b) swelling of said primary particles with a liquid comprising at least an additional charge of at least one of monomer, oligomer, and a cross-linker;
   c) destabilization by adding at least one of a salt, acid and base and concomitant application of shear until agglomerates of the particles of the desired size are formed; and
   d) polymerization of the agglomerates to form the macro porous micro-clusters,
   wherein in step c) the shear rate, expressed in 1/second, and the ionic strength as given by the concentration of at least one of salt, acid and base, expressed in mol/l, are adapted by measuring the phase diagram and selecting the shear rate and ionic strength to be both at or above the line of the phase boundary and in the gel phase therein.

2. The method according to claim 1, wherein for the measurement of the phase diagram the critical ionic strength value for no shear, the critical shear value for no salt/acid/base as well as at least one ionic strength value for a determined shear or at least one critical shear value for a determined ionic strength is determined, and the phase boundary is determined from these values using a numerical fitting.

3. The method according to claim 1, wherein in step c) at least one of a salt, acid and base is added in an extent such that its concentration in a suspension comprising the particles is above the critical coagulation concentration,
   or wherein in step c) concentration of at least one of salt, acid and base is chosen to be in the range of 1/10 to 1/2 of the critical coagulation concentration.

4. A method for producing macro porous micro-clusters comprising at least the following individual steps in given order:
   a) synthesis of dispersed cross-linked polymeric latex primary particles starting from at least one monomer or oligomer;
   b) swelling of said primary particles with a liquid comprising at least an additional charge of at least one of monomer, oligomer, and a cross-linker;
   c) destabilization by adding at least one of a salt, acid and base and concomitant application of shear until agglomerates of the particles of the desired size are formed;
   d) polymerization of the agglomerates to form the macro porous micro-clusters,
   wherein the shear in step c) is generated by passing the fluid through at least one micro-channel.

5. The method according to claim 1, wherein in step c) a shear rate in the range of 200-4000 1/second is applied,
   and/or wherein in in step c) a shear rate in the range from $1 \times 10^5$ to $1.7 \times 10^6$ 1/s is applied.

6. The method according to claim 1, wherein in step c) the concentration of at least one of salt, acid and base, at least at the end of the step, is twice as high as the critical coagulation concentration.

7. The method according to claim 1, wherein in step c) the concentration of at least one of salt, acid and base is increased over time.

8. The method according to claim 1, wherein step c) is carried out for a time span of at least 5 minutes.

9. The method according to claim 1, wherein step d) is carried out for a time span of at least 1 hour.

10. The method according to claim 1, wherein the primary particles are core shell particles with a hard core.

11. The method according to claim 1, wherein in step b) a mixture of monomers or oligomers, together with a cross-linker system, is added, to the suspension obtained in step a).

12. The method according to claim 1, wherein in step c) a solid volume fraction below 10% is used.

13. The method according to claim 1, wherein the monomers and/or oligomers as used in at least one of step a) and b) are selected from the group forming nanoparticles using emulsion or mini-emulsion based methods.

14. The method according to claim 1, wherein the generated macro porous micro-clusters are surface functionalized, wherein the surface functionalization is generated by the functionalization agent present in at least one of: step b) and a surface functionalization step carried out before or after step d).

15. The method according to claim 1, wherein the generated macro porous micro-clusters are coated by a functional gel.

16. A macro porous micro-cluster as obtained by a method according to claim 1, wherein said macro porous micro-cluster is essentially free from pores with a size below 20 nm.

17. The macro porous micro-cluster according to claim 16, wherein said macro porous micro-cluster has a radius of gyration in the range of 10-100 μm.

18. The macro porous micro-cluster according to claim 16, wherein said macro porous micro-cluster has a surface area SBET in the range of 5-30 m² per gram.

19. Use of macro porous micro-clusters according to claim 16 for the separation of chemical compounds, with molecular weights in the range of 10-200 Dalton or of biopharmaceuticals.

20. The method according to claim 1, wherein step a) involves the synthesis of dispersed cross-linked polymeric latex primary particles starting from at least one monomer or oligomer based on at least one of styrene, acrylic, and vinyl acetate monomers in an emulsion polymerization.

21. The method for producing macro porous micro-clusters according to claim 1, wherein in step c) wherein for the measurement of the phase diagram the critical ionic strength value for no shear, the critical shear value for no salt/acid/base as well as at least one ionic strength value for a determined shear or at least one critical shear value for a determined ionic strength is determined, and the phase boundary is determined from these values using a numerical, quadratic fitting, to determine the parameters a, b and c of the formula, wherein S is the shear rate and I is the ionic strength:

$$S_{fit} = a\ I^2 + b\ I + c$$

and selecting the shear rate (S) and the ionic strength (I) for step c) such that $$S(I) \geq S_{fit}(I),$$

wherein the shear rate (S) and the ionic strength (I) for step c) are chosen such that $$S(I) > S_{fit}(I).$$

22. The method according to claim 1, wherein in step c) the concentration of at least one of salt, acid and base is chosen to be in the range of 1/4 to 1/3 of the critical coagulation concentration, wherein to eliminate undesired aggregate formation a salt/acid/base solution with a concentration equal to or lower than the corresponding CCC is mixed with the latex solution is used.

23. The method according to claim 4, wherein the shear in step c) is generated by passing the fluid through at least one micro-channel, which is a homogenizer with a z-shape of a rectangular cross-section, with a length of $3 \times 10^{-3}$–$7 \times 10^{-3}$ m, and a cross-sectional area of $3 \times 10^{-8}$–$7 \times 10^{-8}$ m$^2$, under conditions of up to $1.7 \cdot 10^6$ l/s at up to 170 bar, with water.

24. The method according to claim 1, wherein in step c) a shear rate in the range of 300-3000 1/second is applied, if aggregation is performed under fully destabilized Diffusion-Limited Cluster Aggregation conditions,
and/or wherein in in step c) a shear rate in the range from $5 \times 10^5$ up to $1.7 \times 10^6$ l/s is applied, if aggregation is performed under partially destabilized Reaction-Limited Cluster Aggregation conditions.

25. The method according to claim 1, wherein in step c) the concentration of at least one of salt, acid and base, at least at the end of the step, is 10 times as high as the critical coagulation concentration if aggregation is performed under fully destabilized Diffusion-Limited Cluster Aggregation conditions.

26. The method according to claim 1, wherein in step c) the concentration of at least one of salt, acid and base is increased over time, by at least two successive gradient salt/acid/base addition steps, wherein already the first adding of salt/acid/base leads to a concentration of the salt/acid/base in the suspension above the critical coagulation concentration, if aggregation is performed under fully destabilized Diffusion-Limited Cluster Aggregation conditions.

27. The method according to claim 1, wherein step c) is carried out for a time span in the range of 30-300 minutes, if aggregation is performed under fully destabilized Diffusion-Limited Cluster Aggregation conditions.

28. The method according to claim 1, wherein step d) is carried out for a time span of at least 10 hours, wherein a temperature of at least 60° C. is used in the suspension.

29. The method according to claim 1, wherein the primary particles are core shell particles with a hard core, which is at least 15% cross-linked, and a soft shell, which is in the range of 1-5% cross-linked wherein the diameter of the primary particles is in the range of 75-180 nm, and wherein the core diameter of the primary particles is in the range of 70-150 nm.

30. The method according to claim 1, wherein in step b) a mixture of monomers or oligomers, of the same type as the ones used in step a), together with a cross-linker system, in approximately the same amount as the monomers/polymers, chosen to be divinylbenzene, for styrene and its derivatives, and/or acrylic monomers, including ethyleneglycoldimethacrylate for MMA and vinyl acetate, and optionally with a functional initiator, is added, including drop wise added to the suspension obtained in step a).

31. The method according to claim 1, wherein in step c) a solid volume fraction below 1-9% is used, if aggregation is performed under fully destabilized Diffusion-Limited Cluster Aggregation conditions,
and/or wherein in in step c) a solid volume fraction in the range of 5-25% is used, if aggregation is performed under partially destabilized Reaction-Limited Cluster Aggregation conditions.

32. The method according to claim 1, wherein the monomers and/or oligomers as used in step a) and/or b) are selected from the group forming nanoparticles using emulsion or mini-emulsion based methods, based on at least one of styrene, acrylic, and vinyl acetate monomers, or their derivatives.

33. The method according to claim 1, wherein the generated macro porous micro-clusters are surface functionalized, in that functional groups are grafted onto the surface thereof, wherein the surface functionalization is generated by the functionalization agent present a step b) and/or by a surface functionalization step carried out before or after step b), and wherein the surface functionalization comprises or consists of sulphonate groups, including multiple sulphonate groups.

34. A method for producing macro porous micro-clusters comprising at least the following individual steps in given order:
a) synthesis of dispersed cross-linked polymeric latex primary particles starting from at least one monomer or oligomer;
b) swelling of said primary particles with a liquid comprising at least an additional charge of at least one of monomer, oligomer, and a cross-linker;
c) destabilization by adding at least one of a salt, acid and base and concomitant application of shear until agglomerates of the particles of the desired size are formed;
d) polymerization of the agglomerates to form the macro porous micro-clusters,
wherein the generated macro porous micro-clusters are coated, by at least partially filling cavities thereof, by a functional gel, based on nanoparticles, for ion exchange chromatography, including for anion exchange chromatography, wherein the functional gel is an aminated acrylate-based polymer with which particles are impregnated after step d).

35. A macro porous micro-cluster according to claim 16, having a fractal dimension of in the range of 2.5-3.

36. The macro porous micro-cluster according to claim 16, characterized in that it is essentially free from pores with a size below 50 nm.

37. Use of macro porous micro-clusters according to claim 16 for the separation of chemical compounds, namely small ions, cations or anions, with molecular weights in the range of 10-200 Dalton and/or of biopharmaceuticals, including peptides or monoclonal antibodies, with large molecular weight in the range of 10 000-1 000 000 Dalton, including monoclonal antibodies, wherein the micro-clusters are either directly or after grinding used for chromatographic separation purposes, for ion chromatography, including ion exchange chromatography, including anion exchange chromatography.

38. The method according to claim 1, wherein step b) involves swelling of the primary particles with a liquid comprising at least an additional charge of at least one of monomer, oligomer, and a cross-linker, further comprising functionalization agents.

39. The method according to claim 1, wherein in step c) a solid volume fraction below 10% is used if aggregation is performed under fully destabilized Diffusion-Limited Cluster Aggregation conditions.

40. The method according to claim 1, wherein in in step c) a solid volume fraction below 50% is used.

41. The method according to claim 1, wherein the generated macro porous micro-clusters are surface functionalized, in that functional groups are grafted onto the surface thereof, wherein the surface functionalization is generated by the functionalization agent present a step b) and/or by a surface functionalization step carried out before or after step b), and wherein the surface functionalization comprises or consists of branched multiple sulphonate brushes.

42. A macro porous micro-cluster as obtained by a method according to claim 4, wherein said macro porous micro-cluster is essentially free from pores with a size below 20 nm.

43. The macro porous micro-cluster according to claim 42, wherein said micro-cluster has a radius of gyration in the range of 10-100 μm.

44. The macro porous micro-cluster according to claim 42, wherein said micro-cluster has a surface area SBET in the range of 5-30 m$^2$ per gram.

45. Use of macro porous micro-clusters according to claim 42 for the separation of chemical compounds, with molecular weights in the range of 10-200 Dalton or of biopharmaceuticals.

46. A macro porous micro-cluster according to claim 42, having a fractal dimension of in the range of 2.5-3.

47. The macro porous micro-cluster according to claim 42, characterized in that it is essentially free from pores with a size below 50 nm.

48. Use of macro porous micro-clusters according to claim 42 for the separation of chemical compounds, namely small ions, cations or anions, with molecular weights in the range of 10-200 Dalton and/or of biopharmaceuticals, including peptides or monoclonal antibodies, with large molecular weight in the range of 10 000-1 000 000 Dalton, including monoclonal antibodies, wherein the micro-clusters are either directly or after grinding used for chromatographic separation purposes, for ion chromatography, including ion exchange chromatography, including anion exchange chromatography.

49. A method according to claim 1, including the steps of producing macro porous micro-clusters and using the resulting macro porous micro-clusters for the separation of chemical compounds, namely small ions, cations or anions, with molecular weights in the range of 10-200 Dalton and/or of biopharmaceuticals, including peptides or monoclonal antibodies, with large molecular weight in the range of 10 000-1 000 000 Dalton, including monoclonal antibodies, wherein the micro-clusters are either directly or after grinding used for chromatographic separation purposes, for ion chromatography, including ion exchange chromatography, including anion exchange chromatography.

* * * * *